United States Patent
Henning et al.

(10) Patent No.: US 10,017,540 B2
(45) Date of Patent: Jul. 10, 2018

(54) CYCLIC PEPTIDE BINDER AGAINST ONCOGENIC K-RAS

(71) Applicant: CALIFORNIA INSTITUTE OF TECHNOLOGY, Pasadena, CA (US)

(72) Inventors: Ryan K. Henning, Pasadena, CA (US); Ashwin N. Ram, Pasadena, CA (US); Samir Das, Pasadena, CA (US); Arundhati Nag, Pasadena, CA (US); James R. Heath, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/068,528

(22) Filed: Mar. 11, 2016

(65) Prior Publication Data
US 2016/0264627 A1    Sep. 15, 2016

Related U.S. Application Data

(60) Provisional application No. 62/131,670, filed on Mar. 11, 2015.

(51) Int. Cl.
| | | |
|---|---|---|
| *A61K 38/12* | (2006.01) | |
| *A61P 35/00* | (2006.01) | |
| *C07K 7/64* | (2006.01) | |
| *G01N 33/574* | (2006.01) | |
| *C07K 14/82* | (2006.01) | |
| *C07K 7/06* | (2006.01) | |
| *A61K 38/00* | (2006.01) | |

(52) U.S. Cl.
CPC .................. *C07K 7/64* (2013.01); *C07K 7/06* (2013.01); *C07K 14/82* (2013.01); *G01N 33/5748* (2013.01); *A61K 38/00* (2013.01); *G01N 2333/82* (2013.01); *G01N 2333/914* (2013.01); *G01N 2500/04* (2013.01)

(58) Field of Classification Search
CPC ................................ A61K 38/00; A61K 38/12
See application file for complete search history.

(56) References Cited

FOREIGN PATENT DOCUMENTS

WO    WO 2014205317 A2 * 12/2014 ............. C07K 1/047

OTHER PUBLICATIONS

Baines, Antonio T. et al.; "Inhibition of Ras for cancer treatment: the search continues"; Future Med Chem.; Oct. 2011; 3(14); pp. 1787-1808.
Bamford, S. et al.; "The COSMIC (Catalogue of Somatic Mutations in Cancer) database and website"; British Journal of Cancer; 2004; 91; pp. 355-358.
Das, Samir et al.; "A General Synthetic Approach for Designing Epitope Targeted Macrocyclic Peptide Ligands"; Angew. Chem. Int. Ed.; 2015; 54; 7pp.
Downward, Julian; "Targeting Ras Signalling Pathways in Cancer Therapy"; Nature Reviews; Cancer; vol. 3; Jan. 2003; pp. 11-22.
Nag, Arundhati et al.; "A Chemical Epitope-Targeting Strategy for Protein Capture Agents: The Serine 474 Epitope of the Kinase Akt2**"; Angew. Chem. Int. Ed. Engl.; Dec. 23, 2013; 52(52); pp. 13975-13979.
Ostrem, Jonathan M. et al.; "K-Ras(G12C) inhibitors allosterically control GTP affinity and effector interactions"; Nature; vol. 503; Nov. 28, 2013; 14pp.
Schubbert, Suzanne et al.; "Hyperactive Ras in developmental disorders and cancer"; Nature Reviews; Cancer; vol. 7; Apr. 2007; pp. 295-308.
Terpe, K.; "Overview of tag protein fusions: from molecular and biochemical fundamentals to commercial systems"; Appl. Microbiol. Biotechnol.; Jan. 2003; 60(5); pp. 523-533.
Toure, Momar et al.; "Small-Molecule PROTACS: New Approaches to Protein Degradation and Crews"; Angew. Chem. Int. Ed.; 55; 2016; pp. 2-10.

* cited by examiner

*Primary Examiner* — Hasan Ahmed
*Assistant Examiner* — Kaipeen Yang
(74) *Attorney, Agent, or Firm* — Pabst Patent Group LLP

(57) ABSTRACT

Cyclic peptides represented by (Formula 1)

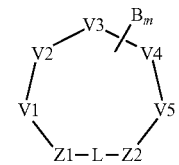

selectively bind the oncoprotein K-Ras G12D in vitro and in cellulo, where Z1 and Z2 are each L-propargylglycine (Pra), azidoornithine (OrnN3), or L-azidolysine (Az4), and V1-V2-V3-V4-V5 is an amino acid variable region having a sequence selected from the group consisting of SEQ ID NOs: 1-20.

11 Claims, 26 Drawing Sheets
(25 of 26 Drawing Sheet(s) Filed in Color)

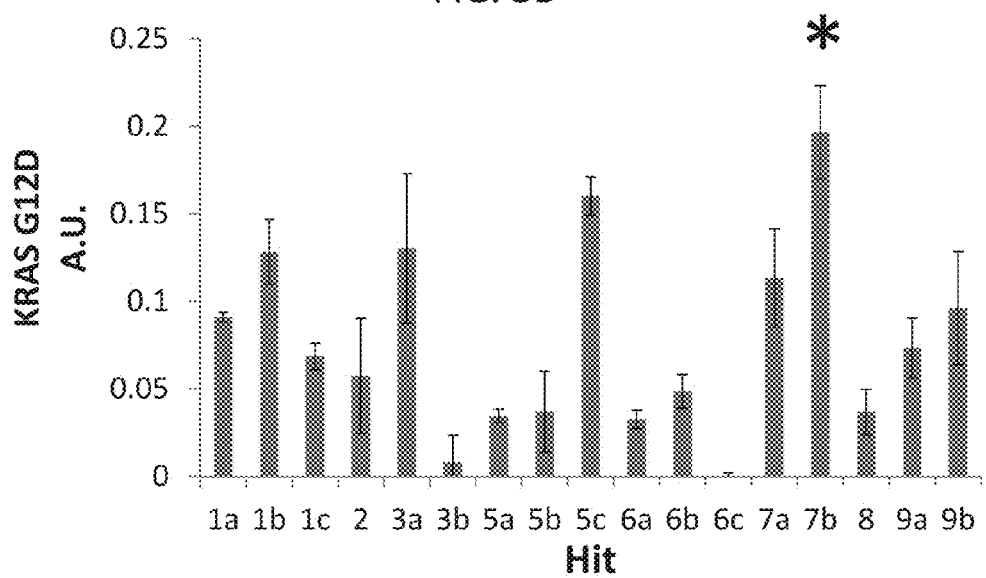

7b1: Pra-LRGDR-Az4-PEG-Biotin

Molecular Weight: 1293.6 m/z

7b2: Az4-LRGDR-Pra-PEG-Biotin

Molecular Weight: 1293.6 m/z

7b3: Pra-LRGDR-Az3-PEG-Biotin

Molecular Weight: 1279.5 m/z

7b4: Pra-VRGDR-Az4-PEG-Biotin

Molecular Weight: 1279.5

7b5: Pra-LRGPR-Az4-PEG-Biotin

Molecular Weight: 1275.6 m/z

7b6: Pra-LRGER-Az4-PEG-Biotin

Molecular Weight: 1307.6 m/z

7b7: Pra-L(homoR)GDR-Az4-PEG-Biotin

Molecular Weight: 1307.6 m/z

7b8: Pra-LRGD(homoR)-Az4-PEG-Biotin

Molecular Weight: 1307.6 m/z

7b9: Pra-L(guanidinoF)GDR-Az4-PEG-Biotin

Molecular Weight: 1341.6 m/z

7b10: Pra-LRGD(guanidinoF)-Az4-PEG-Biotin

Molecular Weight: 1341.6 m/z

7b11: Pra-LRGNR-Az4-PEG-Biotin

Molecular Weight: 1292.6 m/z

7b12: Pra-LRGQR-Az4-PEG-Biotin

Molecular Weight: 1306.6 m/z

7b14: Pra-LRGAR-Az4-PEG-Biotin

Molecular Weight: 1249.6 m/z

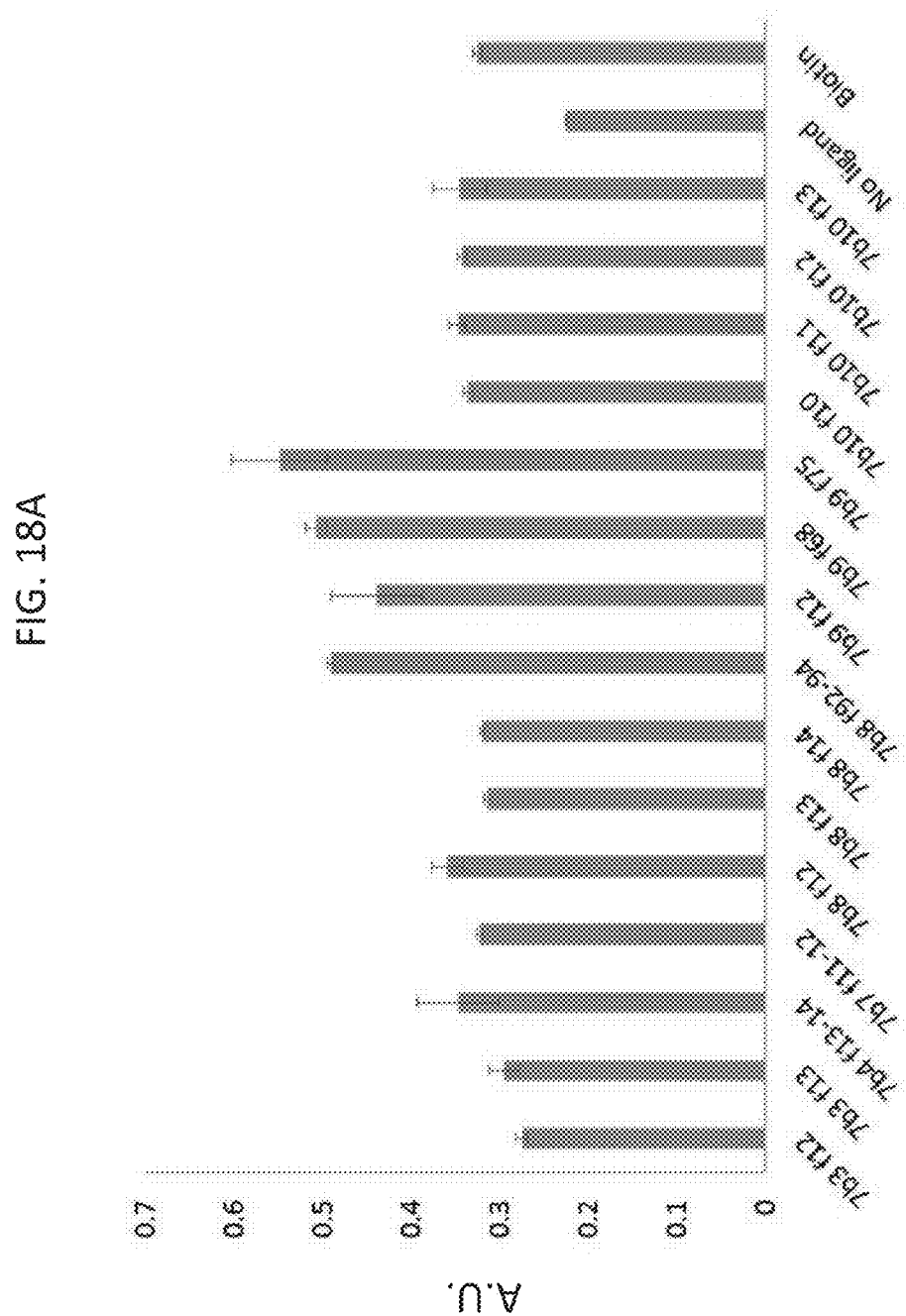
Single point ELISA assay showing relative differences in binding to KRAS G12D between various hit peptides.

7b10 Structure

7b5

SEQUENCE LISTING

```
<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Asp Glu Thr Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Ser Glu Glu Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Glu Glu Gly Gly
1               5

<210> SEQ ID NO 4
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 4

Glu Gly Thr Gly Thr
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Glu Gln Gly Glu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Gly Glu Gln Glu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Arg Gly Asp Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Glu Lys Pro Pro
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Leu Thr Phe Gly
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Arg Gly Asp Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Arg Gly Pro Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Arg Gly Glu Arg
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine

<400> SEQUENCE: 13

Leu Arg Gly Asp Arg
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Homoarginine

<400> SEQUENCE: 14

Leu Arg Gly Asp Arg
1               5

<210> SEQ ID NO 15
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Guanidino phenylalanine

<400> SEQUENCE: 15

Leu Phe Gly Asp Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Guanidino phenylalanine

<400> SEQUENCE: 16

Leu Arg Gly Asp Phe
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Guanidino phenylalanine

<400> SEQUENCE: 17

Leu Arg Gly Ala Phe
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Arg Gly Asn Arg
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Arg Gly Gln Arg
1               5
```

```
<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Arg Gly Ala Arg
1               5

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: L-propargylglycine

<400> SEQUENCE: 21

Thr Glu Tyr Lys Leu Val Val Val Gly Ala Gly Gly Xaa Gly Lys Ser
1               5                   10                  15

Ala Leu Thr Ile Gln
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: L-propargylglycine

<400> SEQUENCE: 22

Thr Glu Tyr Lys Leu Val Val Val Gly Ala Asp Gly Xaa Gly Lys Ser
1               5                   10                  15

Ala Leu Thr Ile Gln
            20

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Leu Ala Pro Tyr Ile Pro
1               5

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Gly Arg Lys Lys Arg Arg Gln Arg Arg Pro Pro Gln Gln
1               5                   10

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: MOD_RES
<222> LOCATION: (13)..(13)
<223> OTHER INFORMATION: L-propargylglycine, azidoornithine or L-
      azidolysine

<400> SEQUENCE: 25

Thr Glu Tyr Lys Leu Val Val Val Gly Ala Gly Gly Xaa Gly Lys Ser
1               5                   10                  15

Ala Leu Thr Ile Gln
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: L-propargylglycine, azidoornithine or L-
      azidolysine

<400> SEQUENCE: 26

Thr Glu Tyr Lys Leu Val Val Val Gly Ala Asp Gly Xaa Gly Lys Ser
1               5                   10                  15

Ala Leu Thr Ile Gln
            20

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: L-azidolysine

<400> SEQUENCE: 27

Xaa Leu Arg Gly Asp Arg Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: L-azidolysine
<220> FEATURE:
<221> NAME/KEY: MOD_RES
<222> LOCATION: (7)..(7)
<223> OTHER INFORMATION: L-propargylglycine

<400> SEQUENCE: 28

Lys Leu Arg Gly Asp Arg Xaa
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: Azidoornithine

<400> SEQUENCE: 29

Xaa Leu Arg Gly Asp Arg Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: L-azidolysine

<400> SEQUENCE: 30

Xaa Val Arg Gly Asp Arg Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: L-azidolysine

<400> SEQUENCE: 31

Xaa Leu Arg Gly Pro Arg Lys
1               5
```

```
<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: L-azidolysine

<400> SEQUENCE: 32

Xaa Leu Arg Gly Glu Arg Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (6)..(6)
<223> OTHER INFORMATION: Homoarginine
<220> FEATURE:
<221> NAME/KEY: MOD_RES
<222> LOCATION: (7)..(7)
<223> OTHER INFORMATION: L-azidolysine

<400> SEQUENCE: 33

Xaa Leu Arg Gly Asp Arg Lys
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (3)..(3)
<223> OTHER INFORMATION: Guanidino phenylalanine
<220> FEATURE:
<221> NAME/KEY: MOD_RES
<222> LOCATION: (7)..(7)
<223> OTHER INFORMATION: L-azidolysine

<400> SEQUENCE: 34

Xaa Leu Phe Gly Asp Arg Lys
1               5

<210> SEQ ID NO 35
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (6)..(6)
<223> OTHER INFORMATION: Guanidino phenylalanine
<220> FEATURE:
<221> NAME/KEY: MOD_RES
<222> LOCATION: (7)..(7)
<223> OTHER INFORMATION: L-azidolysine

<400> SEQUENCE: 35

Xaa Leu Arg Gly Asp Phe Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: L-azidolysine

<400> SEQUENCE: 36

Xaa Leu Arg Gly Asn Arg Lys
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (7)..(7)
<223> OTHER INFORMATION: L-azidolysine

<400> SEQUENCE: 37

Xaa Leu Arg Gly Gln Arg Lys
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-propargylglycine
<220> FEATURE:

```
<221> NAME/KEY: MOD_RES
<222> LOCATION: (7)..(7)
<223> OTHER INFORMATION: L-azidolysine

<400> SEQUENCE: 38

Xaa Leu Arg Gly Ala Arg Lys
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 39

His His His His His His
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: May or may not be present

<400> SEQUENCE: 40

Arg Arg Arg Arg Arg Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Peptides
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (3)..(3)
<223> OTHER INFORMATION: Homoarginine
<220> FEATURE:
<221> NAME/KEY: MOD_RES
<222> LOCATION: (7)..(7)
<223> OTHER INFORMATION: L-azidolysine

<400> SEQUENCE: 41

Xaa Leu Arg Gly Asp Arg Lys
1               5
```

CYCLIC PEPTIDE BINDER AGAINST ONCOGENIC K-RAS

CROSS-REFERENCE TO RELATED APPLICATION(S)

The present application claims priority to and the benefit of U.S. Provisional Application Ser. No. 62/131,670 filed on Mar. 11, 2015, the entire contents of which are incorporated herein by reference.

STATEMENT REGARDING FEDERALLY SPONSORED RESEARCH OR DEVELOPMENT

This invention was made with government support under Grant No. CA151819 awarded by the National Institutes of Health. The government has certain rights in the invention.

REFERENCE TO A SEQUENCE LISTING

The instant application contains a Sequence Listing which has been submitted electronically in ASCII format via EFS-Web and is hereby incorporated by reference in its entirety. Said ASCII copy, created on Sep. 14, 2017, is named 593345-ITC-033_.txt and is 12,234 bytes in size.

BACKGROUND

The KRAS oncogene is a member of the Ras family of GTPases that are involved in numerous cellular signaling processes. K-Ras mutations are gain-of-function mutations that are present in up to 30% of all tumors, including as many as 90% of pancreatic cancers. Due to the clinical significance of this protein, many attempts have been made to develop Ras inhibitors, but such attempts have been mostly unsuccessful. This is largely due to the difficulty in outcompeting GTP for the K-Ras binding pocket in cells, and the lack of known allosteric regulatory sites.

SUMMARY

In some embodiments of the present invention, a cyclic peptide that selectively binds K-Ras G12D oncogenic protein is represented by Formula I:

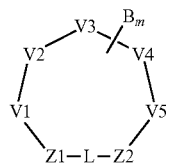

wherein:

Z1 and Z2 are each L-propargylglycine (Pra), azidoornithine (OrnN3), or L-azidolysine (Az4), wherein when L1 is Pra, L2 is OrnN3 or Az4, when L1 is OrnN3 or Az4, L2 is Pra; and V1-V2-V3-V4-V5 is a five amino acid variable region having a sequence selected from the group consisting of SEQ ID NOs: 1-20;

L is a linker moiety; and $B_m$ is a an optional detection group, wherein m is 0 or 1.

In some embodiments of the present invention, a composition for screening peptides that bind to a WT K-Ras epitope using click chemistry includes TEYKLVVVGAGG [Z1]GKSALTIQ (SEQ ID NO: 25), where Z1 is L-propargylglycine (Pra), azidoornithine (OrnN3), or L-azidolysine (Az4).

In some embodiments of the present invention, a composition for screening peptides that bind to a K-Ras G12D epitope using click chemistry includes TEYKLVVVGADG [Z1]GKSALTIQ (SEQ ID NO: 26), where Z1 is L-propargylglycine (Pra), azidoornithine (OrnN3), or L-azidolysine (Az4).

In some embodiments of the present invention, a method of inhibiting K-Ras G12D oncoprotein in a cancer cell expressing K-Ras G12D includes incubating the cancer cell with cyclic peptide of Formula 1 as disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A is a table listing the amino acid sequences (SEQ ID NOs: 1-9, respectively, in order of appearance) of the cyclic peptides corresponding to the 7 hits isolated in the screen of FIG. 2, where SEQ ID NOs: 2 and 3 were two possible sequences from one bead hit and SEQ ID NOs: 5 and 6 were two possible sequences from one bead hit.

FIG. 3B is a graph of the absorbance units (A.U.) corresponding to fluorescence from an ELISA assay measuring the binding of K-Ras G12D to cyclic peptides (1a, 1b, 1c, 2, 3a, 3b, 5a, 5b, 5c, 6a, 6b, 6c, 7a, 7b, 8, 9a, and 9b) synthesized with a polyethylene glycol (PEG) spacer group and biotin tag of Formula 1 having a variable region (V1-V2-V3-V4-V5) selected from SEQ ID NOs. 1-9, according to embodiments of the present invention, in which the synthesized cyclic peptides had up to three (a, b, c) fractions corresponding to epimers; the asterisk highlighted cyclic peptide 7b showed the strongest binding fluorescence.

FIG. 18A is a graph of the relative absorbance units (A.U.) from an ELISA assay measuring binding to K-Ras G12D in the presence of the indicated biotin-tagged cyclic peptide, no ligand/peptide control, and biotin alone, in which various HPLC fractions (f) of the cyclic peptides were assayed as indicated, according to embodiments of the present invention.

DETAILED DESCRIPTION

Figure 1:
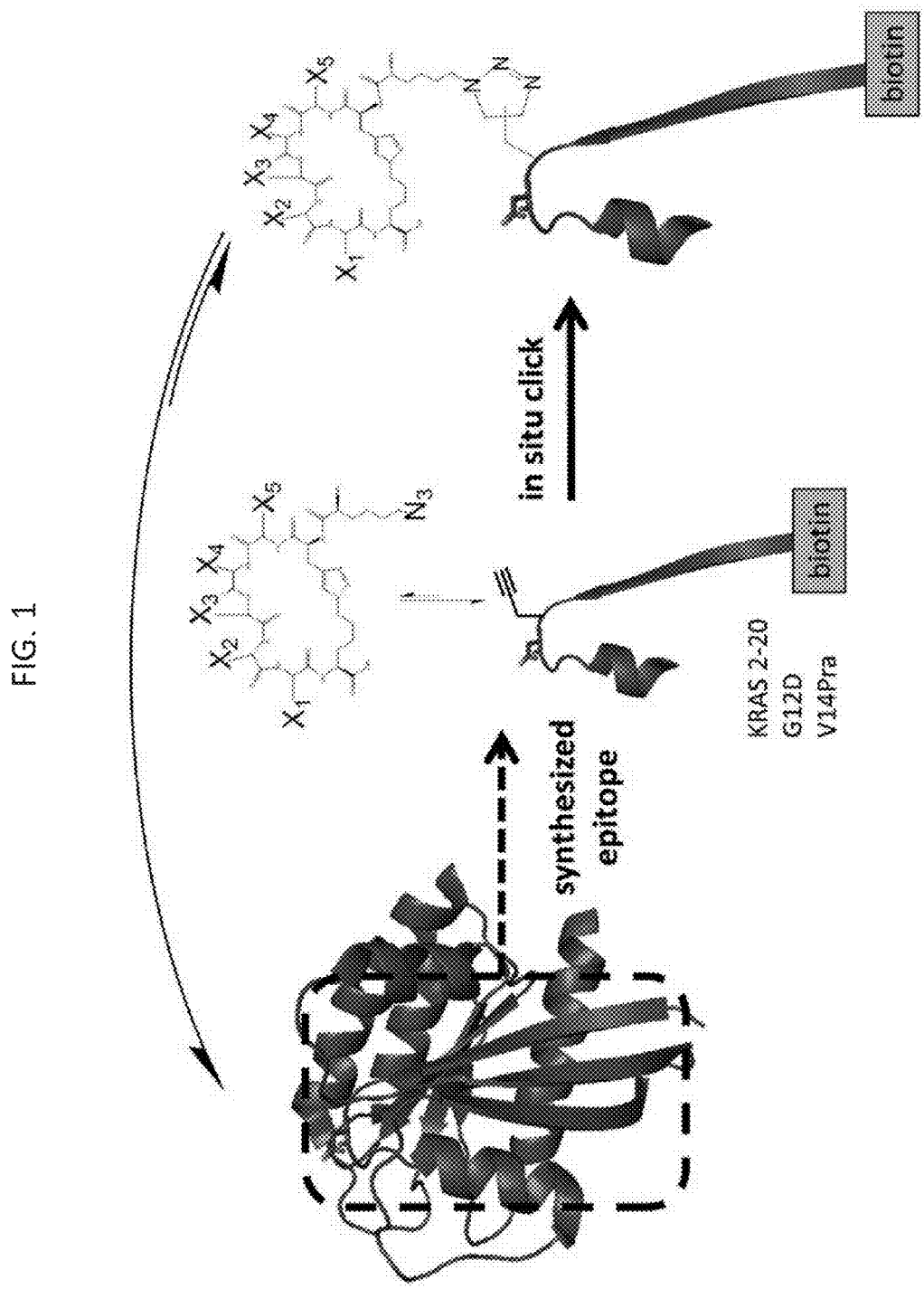
FIG. 1 is a schematic depicting an in situ click chemistry reaction, according to embodiments of the present invention, using a synthetic epitope containing K-Ras residues 2-20 synthesized with a G12D mutation and a propargylglycine (Pra) substitution at valine 14 (V14Pra) conjugated to biotin to identify cyclic peptides that bind the K-Ras epitope. The binding of a peptide from the azide (N3)-terminated one-bead-one-compound (OBOC) cyclic peptide library allows for the bound peptide to covalently bind via azide click chemistry to the biotin tagged K-Ras epitope, allowing for isolation and identification of the cyclic peptide hit. The X1, X2, X3, X4, and X5 represent the variable amino acids, in which the carboxy and amino linkages are shown.

According to aspects of embodiments of the present invention, cyclic peptides of Formula 1 selectively bind the most frequent K-Ras mutation—the oncogenic K-Ras protein having a glycine 12 to aspartic acid (G12D) mutation. The K-Ras G12D mutant accounts for nearly half of all K-Ras oncoproteins. Cyclic peptides according to embodiments of the present invention are capable of binding to the surface of K-Ras G12D, thus circumventing difficulties encountered with inhibitors requiring a binding pocket in K-Ras.

Abbreviations for amino acids are used throughout this disclosure and follow the standard nomenclature known in the art. For example, as would be understood by those of ordinary skill in the art, Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M; Phenylalanine is Phe or F; Proline is Pro or P; Serine is Ser or S; Threonine is Thr or T; Tryptophan is Trp or W; Tyrosine is Tyr or Y; and Valine is Val or V. Synthetic amino acids include L-propargylglycine (Pra); homoarginine (homoArg) or (homoR); guanidinophenylalanine (guanidinoF); L-azidolysine (Az4); and azidoornithine (OrnN3) or (Az3).

Cyclic Peptides that Bind K-Ras G12D

According to some embodiments of the present invention, cyclic peptides that selectively bind to K-Ras G12D may be structurally represented by Formula 1.

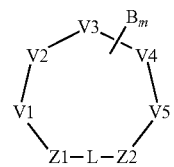

For a cyclic peptide of Formula 1 in which Z1 is a non-naturally occurring amino acid at the amino (N)-terminus, Z2 is a non-naturally occurring amino acid at the carboxy (C)-terminus, and V1-V5 is a 5-amino acid variable region. The 5-amino acid variable region may also be represented as V1-V2-V3-V4-V5.

In some embodiments of the present invention, Z1 and Z2 are not the same and are linked by a triazole group. Z1 and Z2 may each represent a non-naturally occurring amino acid selected from L-propargylglycine (Pra), azidoornithine (OrnN3), or L-azidolysine (Az4), where when Z1 is Pra, Z2 is OrnN3 or Az4, and when Z1 is OrnN3 or Az4, Z2 is Pra. L is a linker moiety. In some embodiments, L is 1,4-triazole linking Z1 and Z2 amino acid groups.

In some embodiments of the present invention, V1-V5 is a five amino acid region having an amino acid sequence selected from SEQ ID NOs: 1-9 as shown in Table 1 or SEQ ID NOs: 10-20 as shown in Table 2.

TABLE 1

| SEQ ID NO | Variable Region (V1-V5) | Example Cyclic Peptide |
|---|---|---|
| 1 | NDETY | 1a, 1b, 1c |
| 2 | PSEEG | 2 |
| 3 | SEEGG | 3a, 3b |
| 4 | EGTGT | K-Ras G12D Epitope Hit |
| 5 | YEQGE | 5a, 5b, 5c |
| 6 | YGEQE | 6a, 6b, 6c |
| 7 | LRGDR | 7a, 7b |
| 8 | QEKPP | 8 |
| 9 | ELTFG | 9a, 9b |

TABLE 2

| SEQ ID NO | Variable Region (V1-V5) | Z1 | Z2 | Example Cyclic Peptide |
|---|---|---|---|---|
| 7 | LRGDR | Pra | Az4 | 7b1 |
| 7 | LRGDR | Az4 | Pra | 7b2 |
| 7 | LRGDR | Pra | OrnN3 | 7b3 |
| 10 | VRGDR | Pra | Az4 | 7b4 |
| 11 | LRGPR | Pra | Az4 | 7b5 |
| 12 | LRGER | Pra | Az4 | 7b6 |
| 13 | L(homoR)GDR | Pra | Az4 | 7b7 |
| 14 | LRGD(homoR) | Pra | Az4 | 7b8 |
| 15 | L(guanidinoF)GDR | Pra | Az4 | 7b9 |
| 16 | LRGD(guanidinoF) | Pra | Az4 | 7b10 |
| 17 | LRGA(guanidinoF) | Pra | Az4 | 7b10-alanine |
| 18 | LRGNR | Pra | Az4 | 7b11 |
| 19 | LRGQR | Pra | Az4 | 7b12 |
| 20 | LRGAR | Pra | Az4 | 7b14 |

Figure 5A:
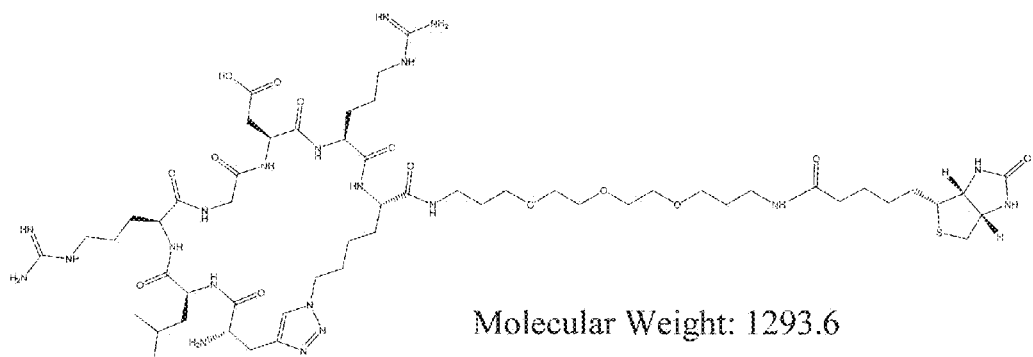
FIG. 5A shows the Formula 1 structure of cyclic peptide 7b1 (Pra-LRGDR-Az4-PEG-Biotin (SEQ ID NO: 27)), according to embodiments of the present invention.
Figure 5B:
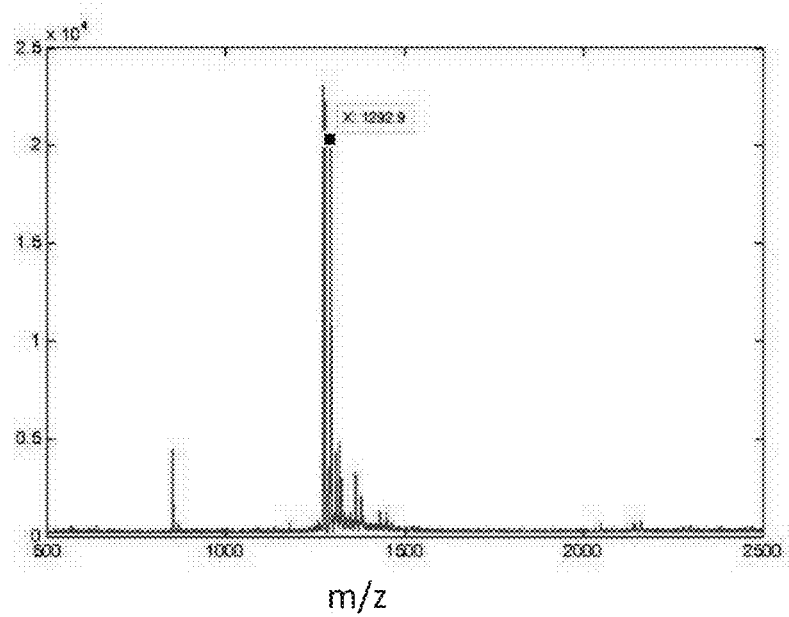
FIG. 5B is a MALDI-TOF mass spectrum for cyclic peptide 7b1 of FIG. 5A, according to embodiments of the present invention.
Figure 6A:
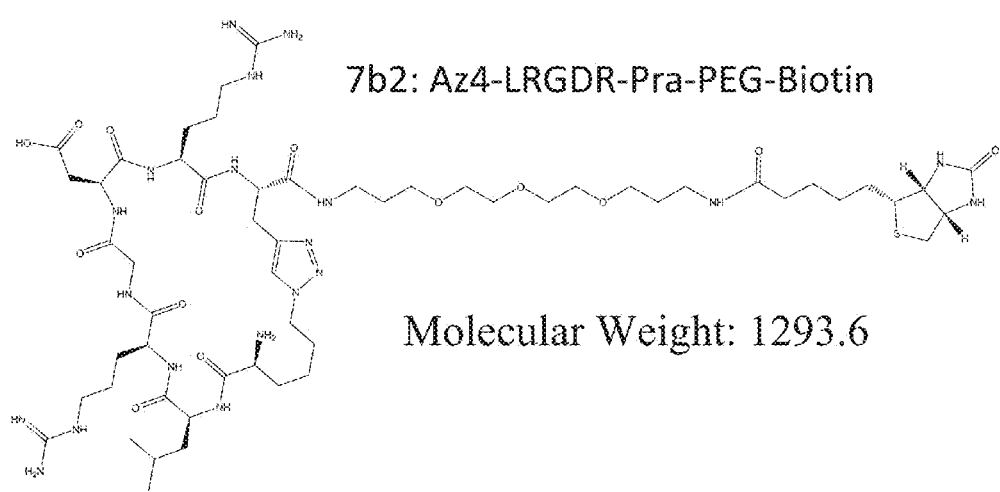
FIG. 6A shows the Formula 1 structure of cyclic peptide 7b2 (Az4-LRGDR-Pra-PEG-Biotin (SEQ ID NO: 28)), according to embodiments of the present invention.
Figure 6B:
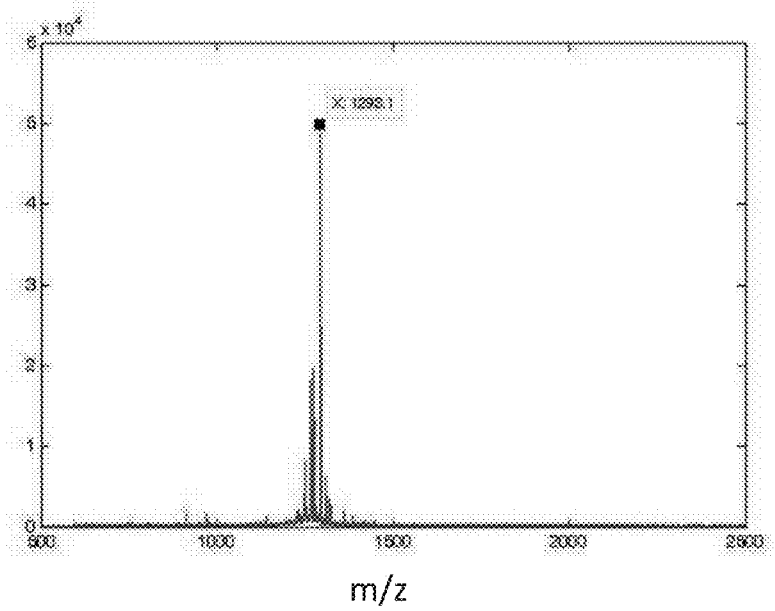
FIG. 6B is a MALDI-TOF mass spectrum for cyclic peptide 7b2 of FIG. 6A, according to embodiments of the present invention.
Figure 7A:
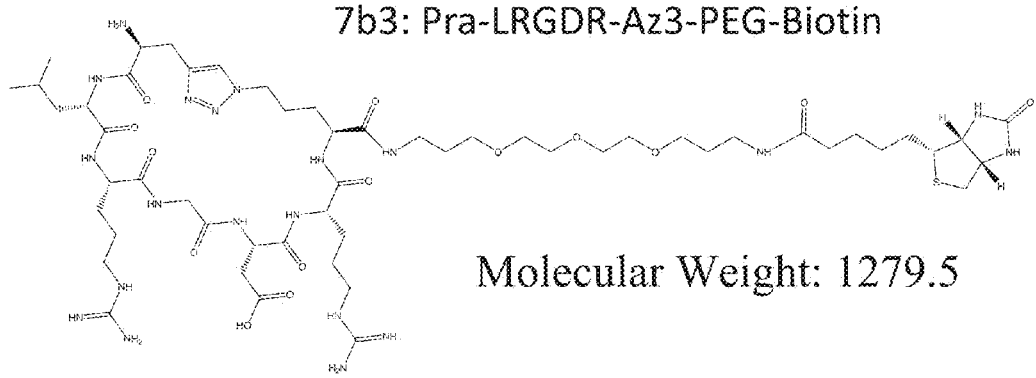
FIG. 7A shows the Formula 1 structure of cyclic peptide 7b3 (Pra-LRGDR-OrnN3-PEG-Biotin (SEQ ID NO: 29)), according to embodiments of the present invention.
Figure 7B:
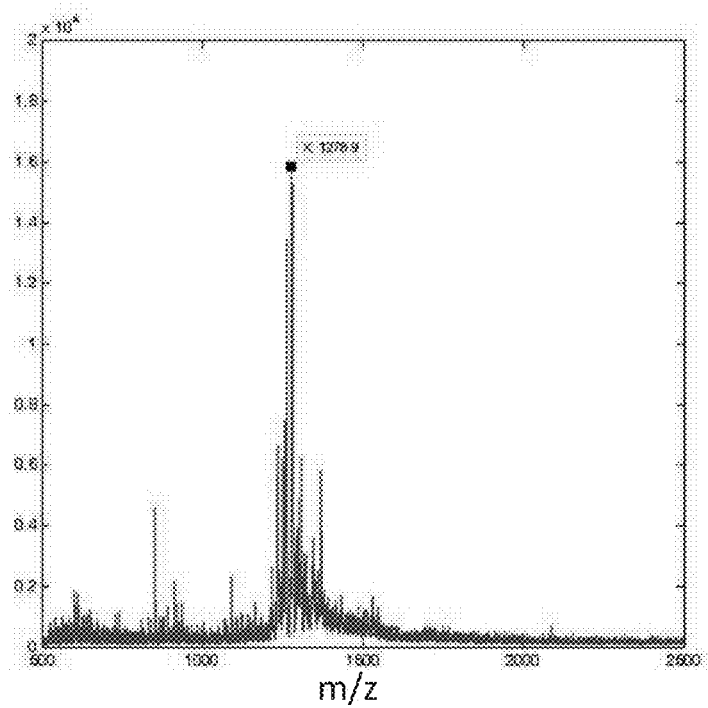
FIG. 7B is a MALDI-TOF mass spectrum for cyclic peptide 7b3 of FIG. 7A, according to embodiments of the present invention.
Figure 8A:
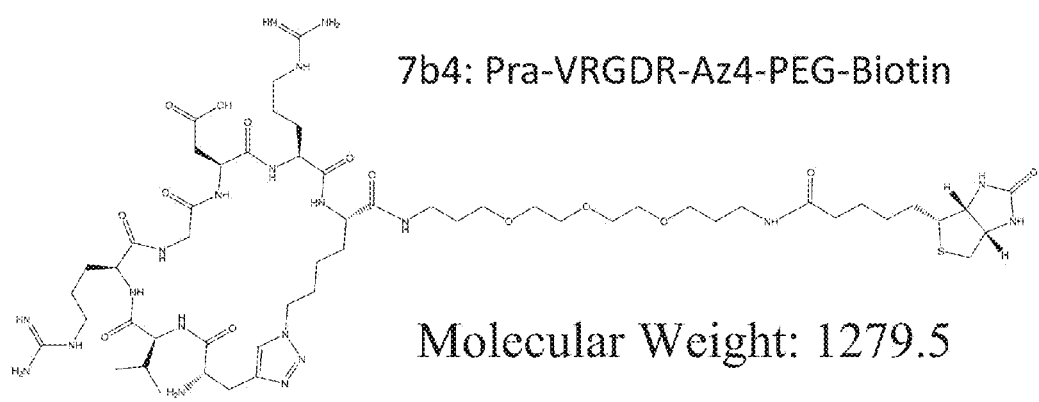
FIG. 8A shows the Formula 1 structure of cyclic peptide 7b4 (Pra-VRGDR-Az4-PEG-Biotin (SEQ ID NO: 30)), according to embodiments of the present invention.
Figure 8B:
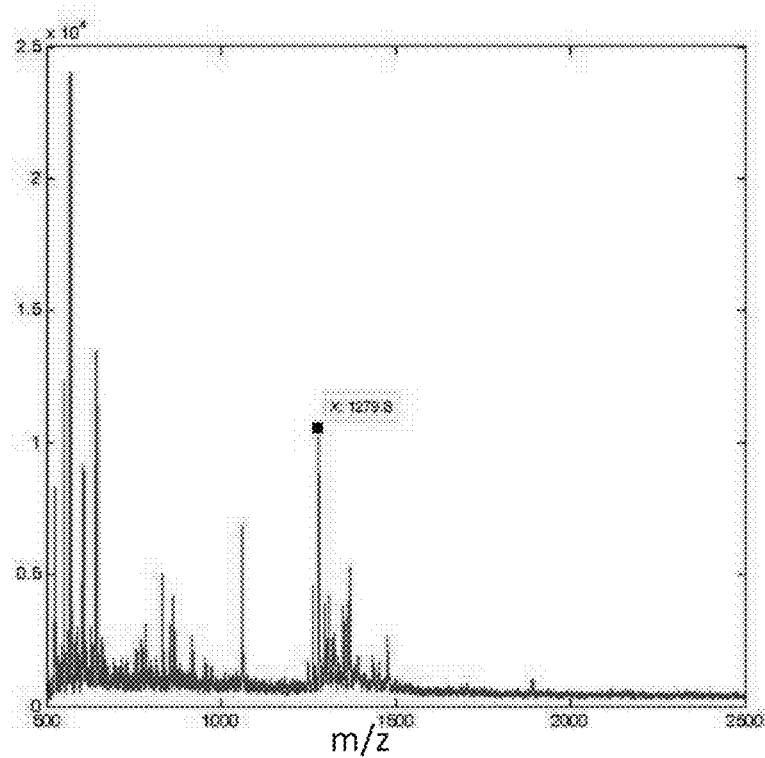
FIG. 8B is a MALDI-TOF mass spectrum for cyclic peptide 7b4 of FIG. 8A, according to embodiments of the present invention.
Figure 9A:
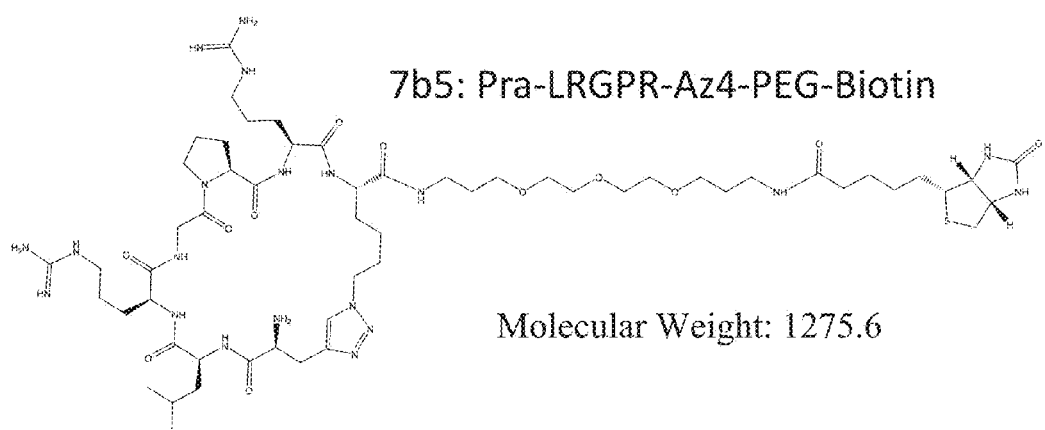
FIG. 9A shows the Formula 1 structure of cyclic peptide 7b5 (Pra-LRGPR-Az4-PEG-Biotin (SEQ ID NO: 31)), according to embodiments of the present invention.
Figure 9B:
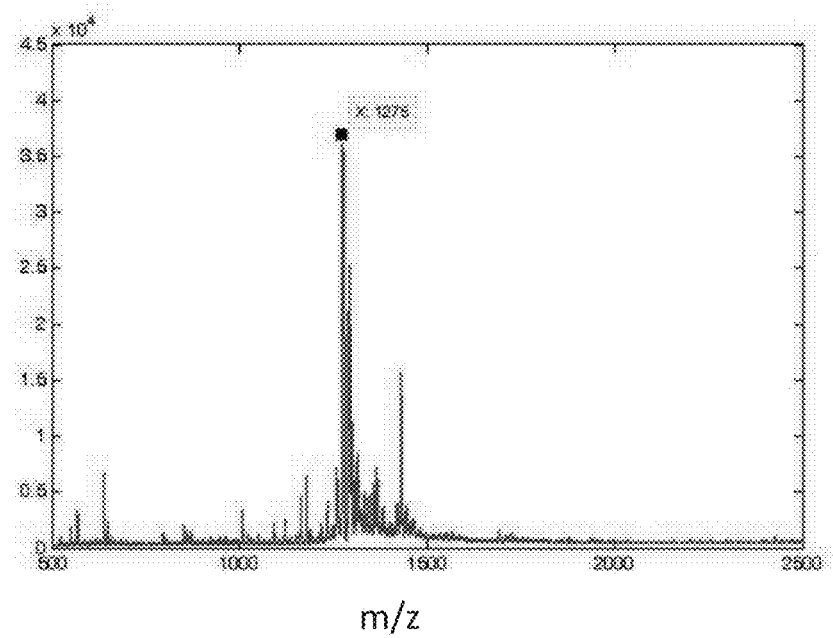
FIG. 9B is a MALDI-TOF mass spectrum for cyclic peptide 7b5 of FIG. 9A, according to embodiments of the present invention.
Figure 10A:
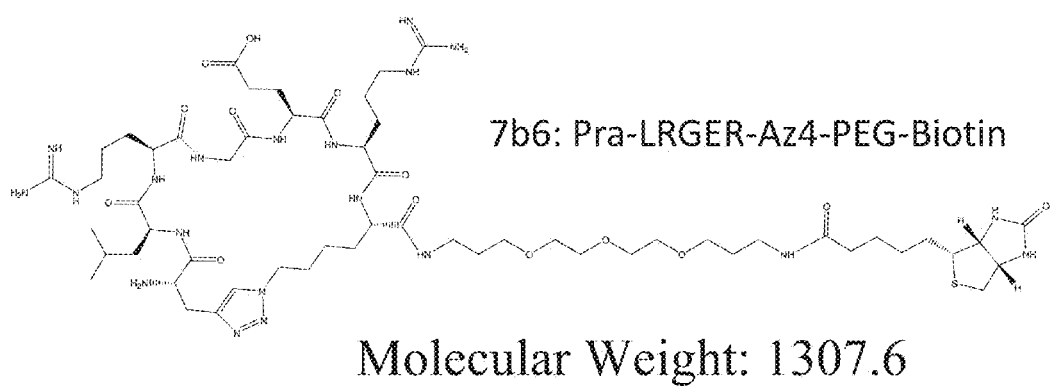
FIG. 10A shows the Formula 1 structure of cyclic peptide 7b6 (Pra-LRGER-Az4-PEG-Biotin (SEQ ID NO: 32)), according to embodiments of the present invention.
Figure 10B:
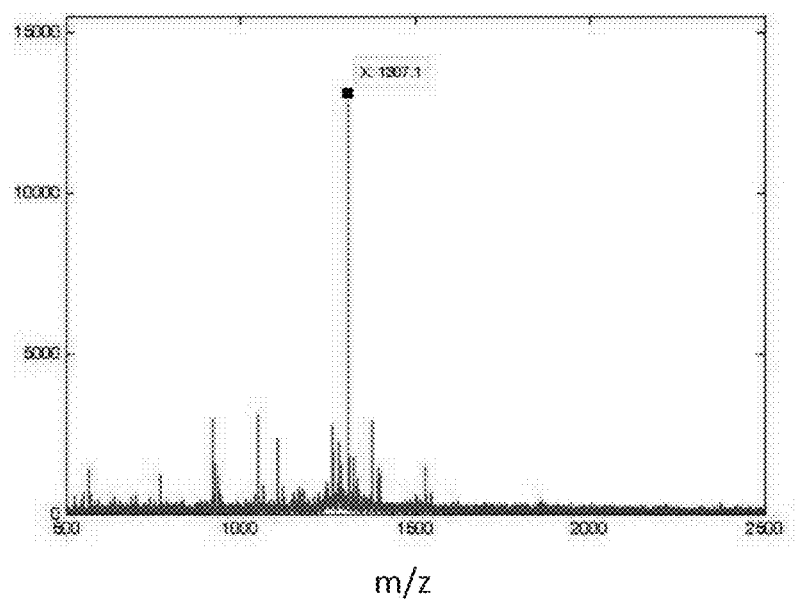
FIG. 10B is a MALDI-TOF mass spectrum for cyclic peptide 7b6 of FIG. 10A, according to embodiments of the present invention.
Figure 11A:
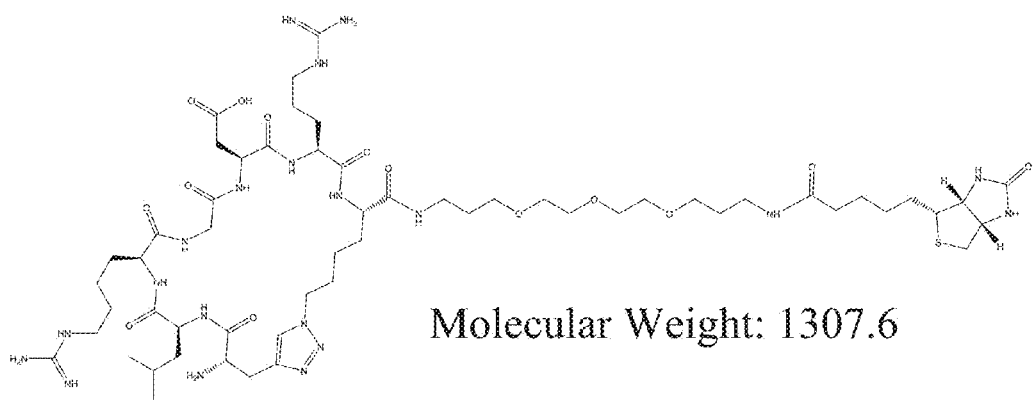
FIG. 11A shows the Formula 1 structure of cyclic peptide 7b7 Pra-L(homoR)GDR-Az4-PEG-Biotin (SEQ ID NO: 41)), according to embodiments of the present invention.
Figure 11B:
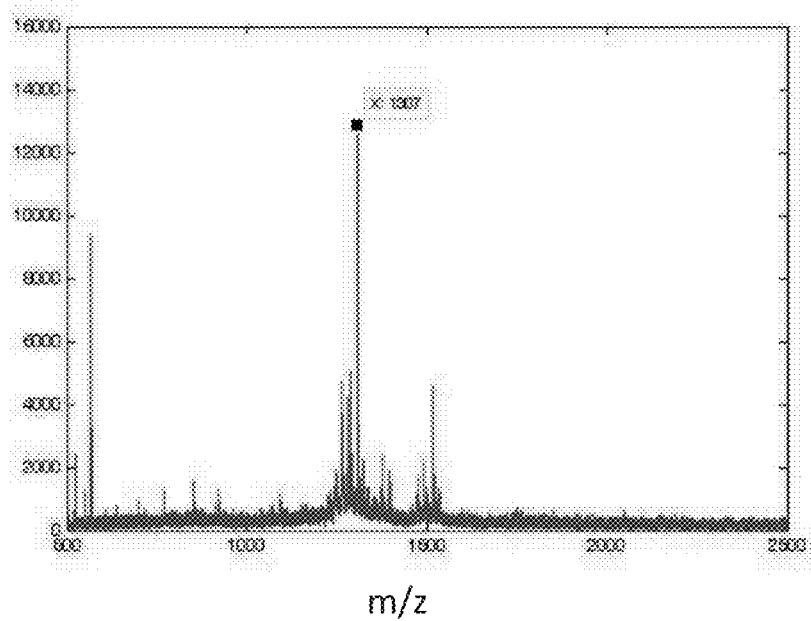
FIG. 11B is a MALDI-TOF mass spectrum for cyclic peptide 7b7 of FIG. 11A, according to embodiments of the present invention.
Figure 12A:
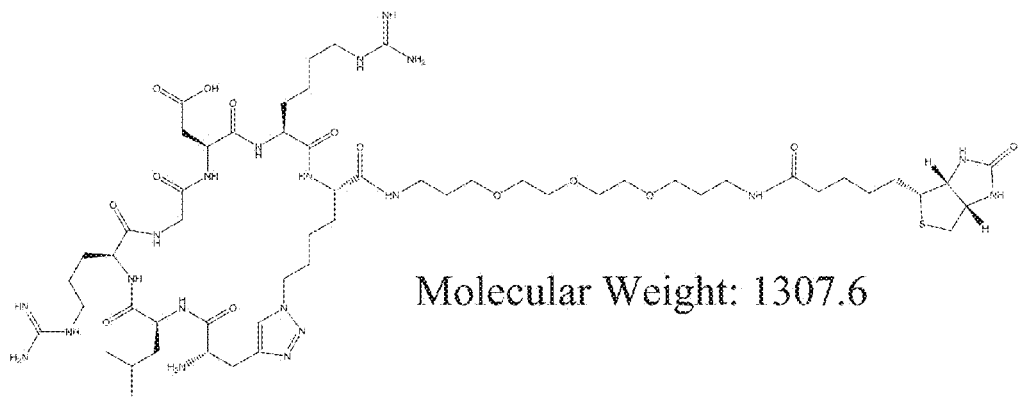
FIG. 12A shows the Formula 1 structure of cyclic peptide 7b8 (Pra-LRGD(homoR)-Az4-PEG-Biotin (SEQ ID NO: 33)), according to embodiments of the present invention.
Figure 12B:
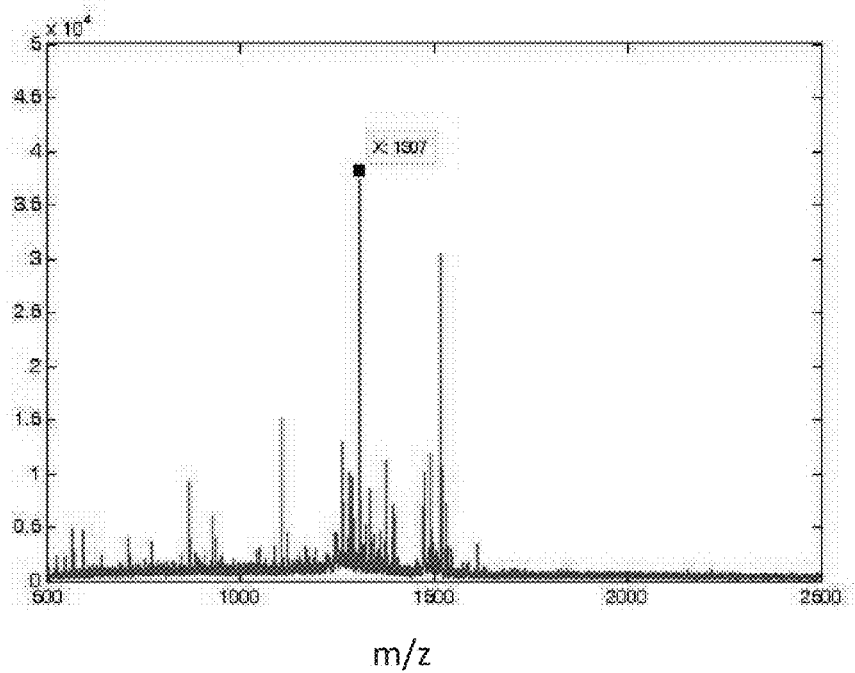
FIG. 12B is a MALDI-TOF mass spectrum for cyclic peptide 7b8 of FIG. 12A, according to embodiments of the present invention.
Figure 13A:
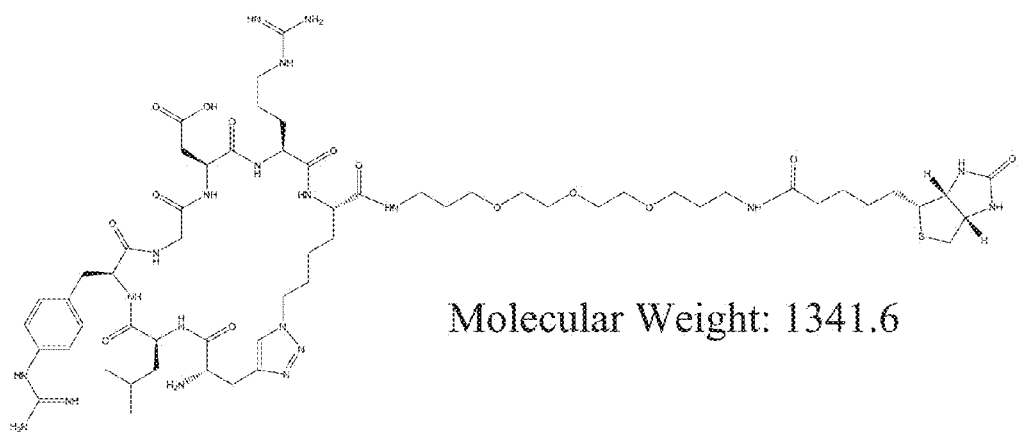
FIG. 13A shows the Formula 1 structure of cyclic peptide 7b9 Pra-L(guanidinoF)GDR-Az4-PEG-Biotin (SEQ ID NO: 34)), according to embodiments of the present invention.
Figure 13B:
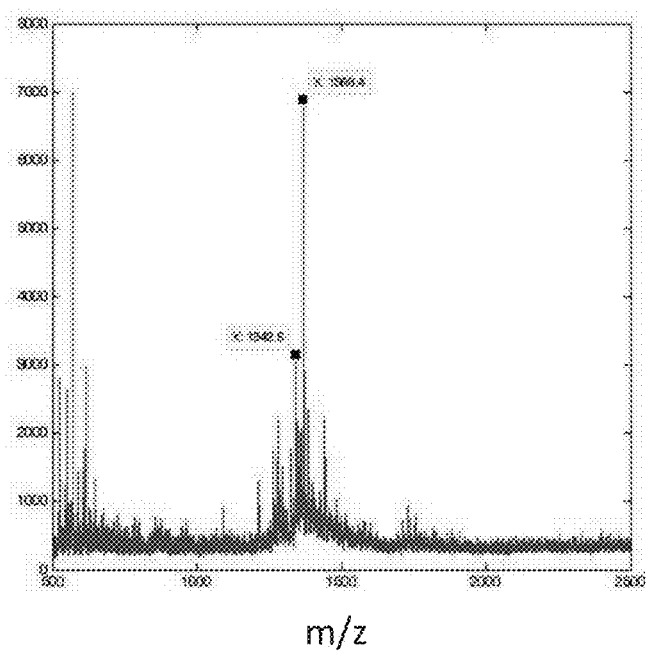
FIG. 13B is a MALDI-TOF mass spectrum for cyclic peptide 7b9 of FIG. 13A, according to embodiments of the present invention.
Figure 14A:
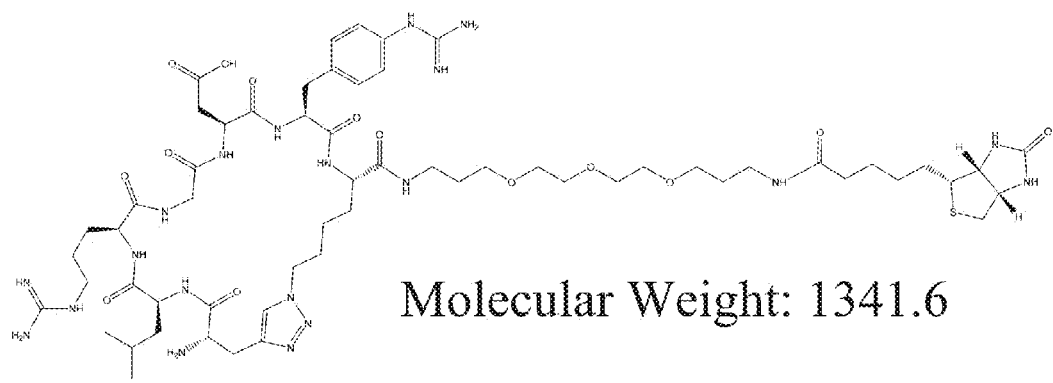
FIG. 14A shows the Formula 1 structure of cyclic peptide 7b10 (Pra-LRGD(guanidinoF)-Az4-PEG-Biotin (SEQ ID NO: 35)), according to embodiments of the present invention.
Figure 14B:
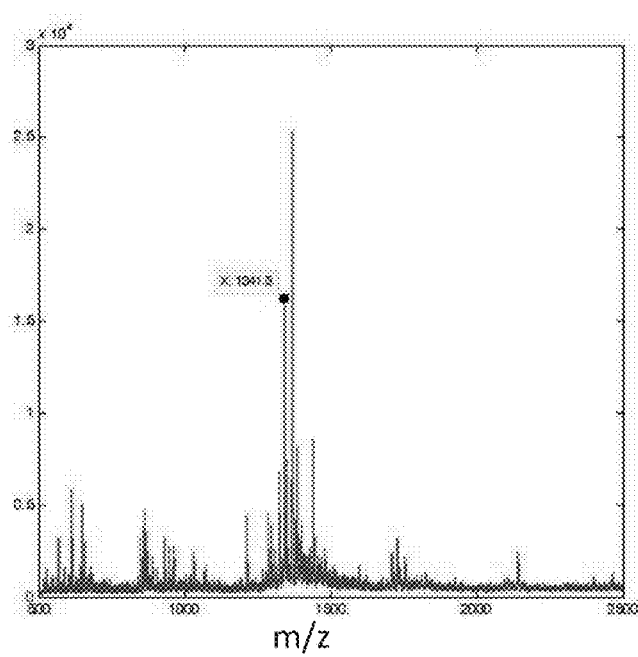
FIG. 14B is a MALDI-TOF mass spectrum for cyclic peptide 7b10 of FIG. 14A, according to embodiments of the present invention.
Figure 15A:
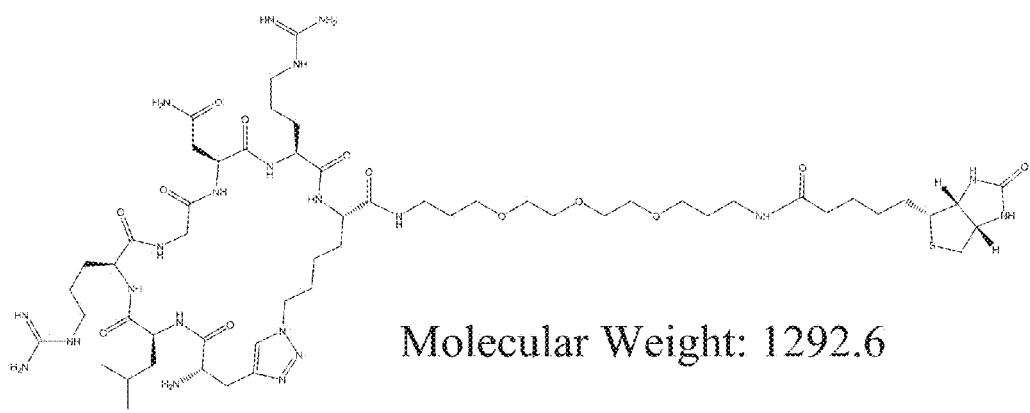
FIG. 15A shows the Formula 1 structure of cyclic peptide 7b11 (Pra-LRGNR-Az4-PEG-Biotin (SEQ ID NO: 36)), according to embodiments of the present invention.
Figure 15B:
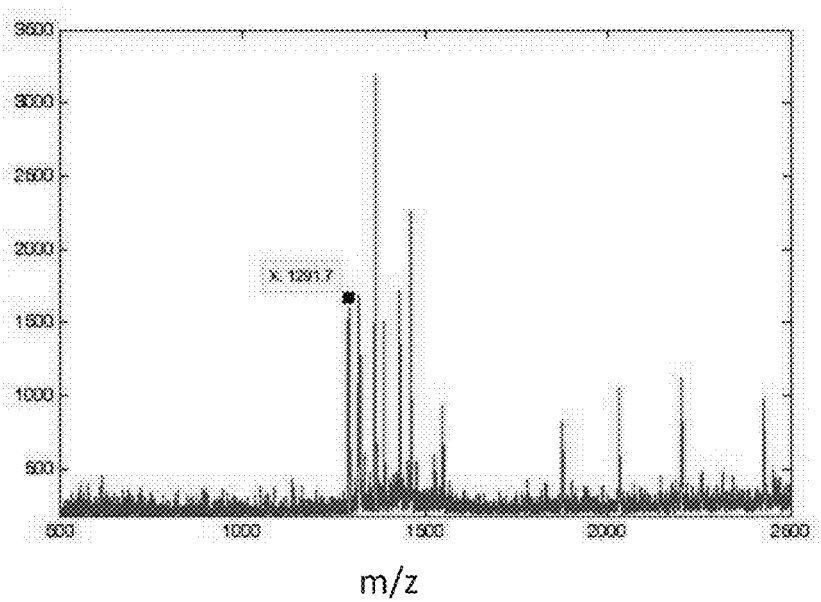
FIG. 15B is a MALDI-TOF mass spectrum for cyclic peptide 7b11 of FIG. 15A, according to embodiments of the present invention.
Figure 16A:
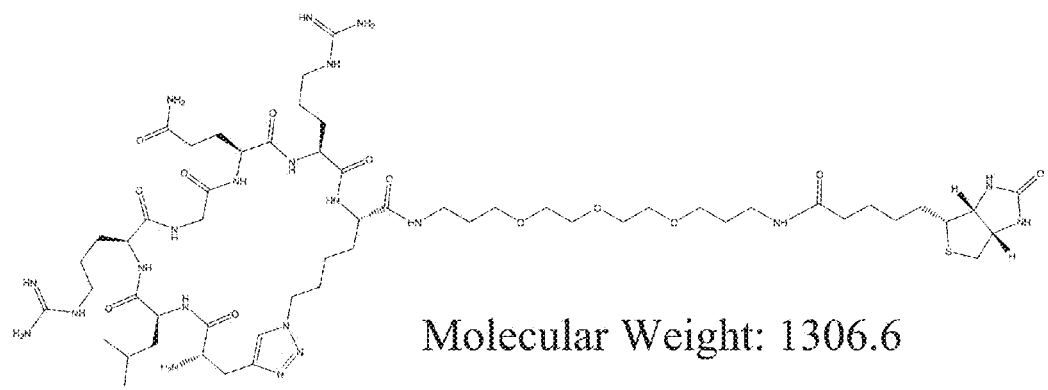
FIG. 16A shows the Formula 1 structure of cyclic peptide 7b12 (Pra-LRGQR-Az4-PEG-Biotin (SEQ ID NO: 37)), according to embodiments of the present invention.
Figure 16B:
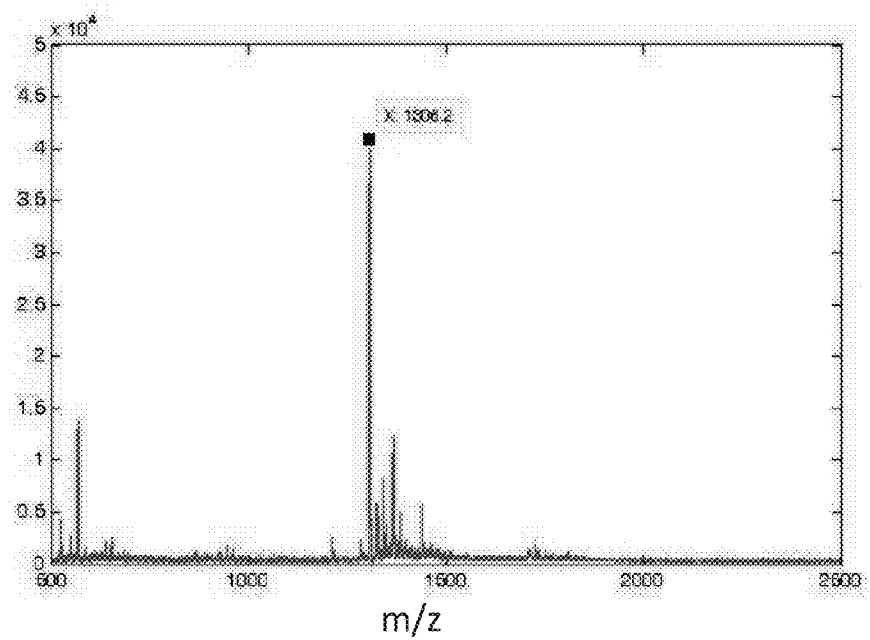
FIG. 16B is a MALDI-TOF mass spectrum for cyclic peptide 7b12 of FIG. 16A, according to embodiments of the present invention.
Figure 17A:
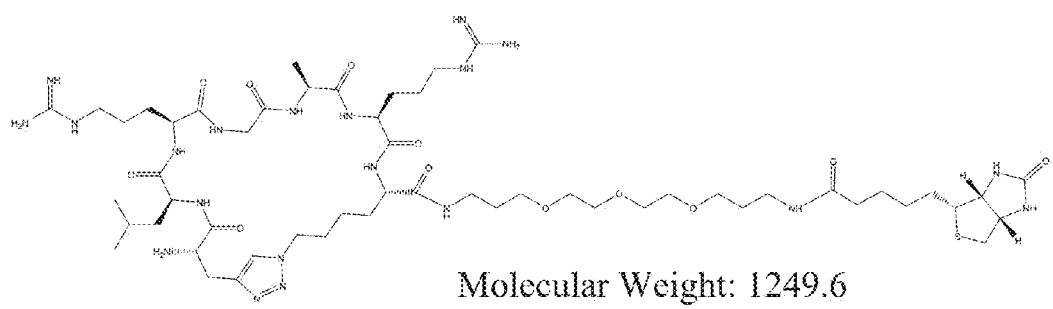
FIG. 17A shows the Formula 1 structure of cyclic peptide 7b14 (Pra-LRGAR-Az4-PEG-Biotin (SEQ ID NO: 38)), according to embodiments of the present invention.
Figure 17B:
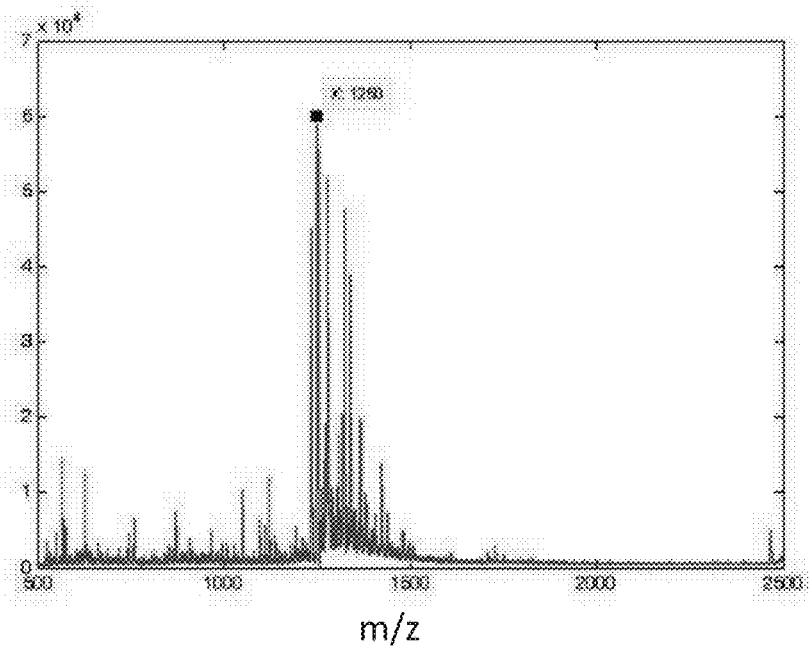
FIG. 17B is a MALDI-TOF mass spectrum for cyclic peptide 7b14 of FIG. 17A, according to embodiments of the present invention.
Figure 18B:
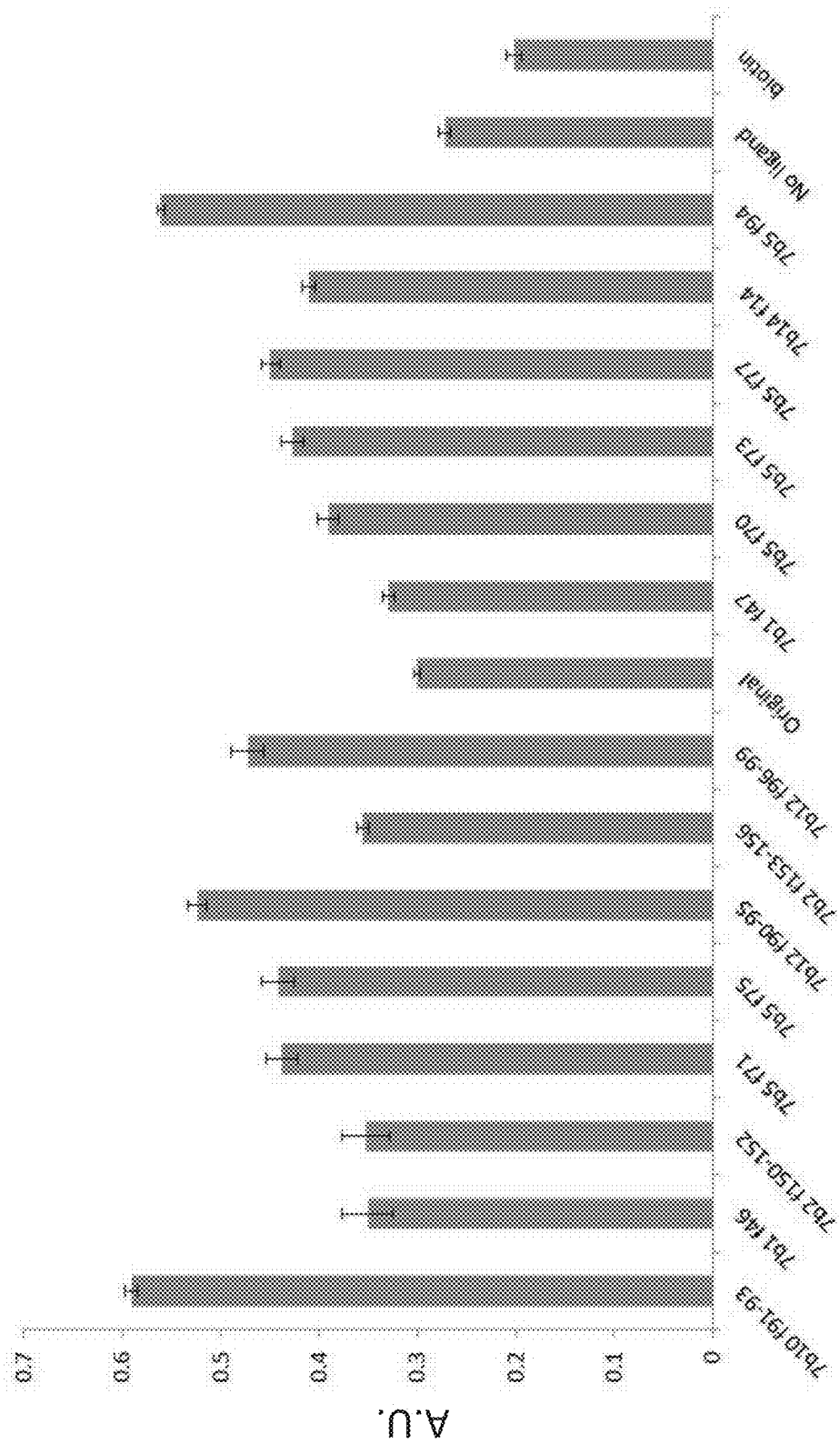
FIG. 18B is a graph of the relative absorbance units (A.U.) from an ELISA assay measuring binding to K-Ras G12D in the presence of the indicated biotin-tagged cyclic peptide, no ligand/peptide control, and biotin alone, in which various HPLC fractions (f) of the cyclic peptides were assayed as indicated, and the "Original" cyclic peptide is 7b, also referred to herein as 7b1, according to embodiments of the present invention.
Figure 18C:
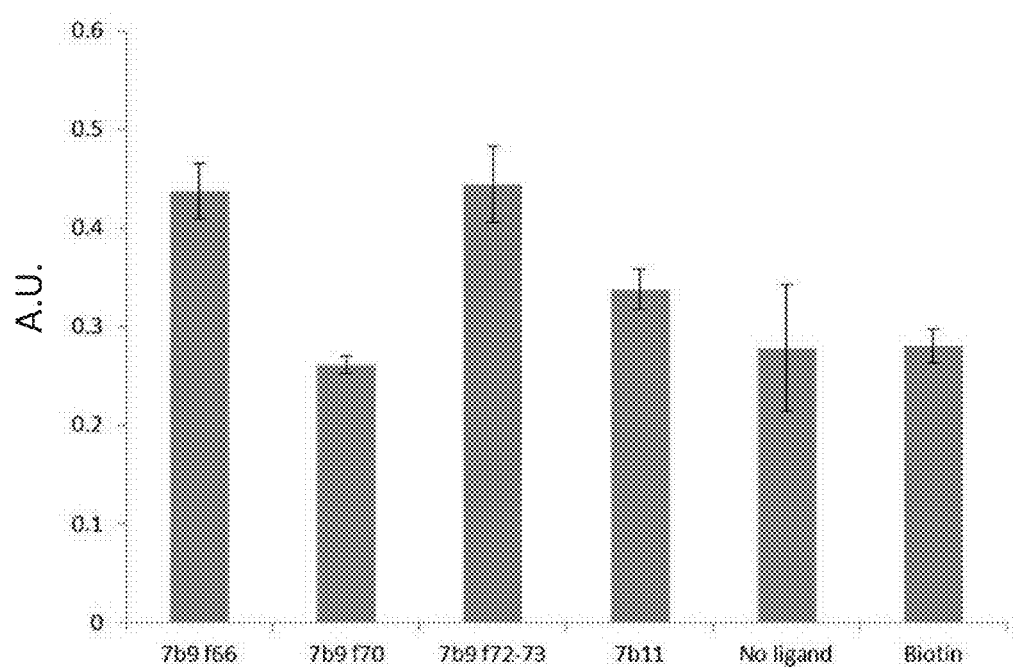
FIG. 18C is a graph of the relative absorbance units (A.U.) from an ELISA assay measuring binding to K-Ras G12D in the presence of the indicated biotin-tagged cyclic peptide, no ligand/peptide control, and biotin alone, in which various HPLC fractions (f) of the cyclic peptides were assayed as indicated, according to embodiments of the present invention.
Figure 19A:
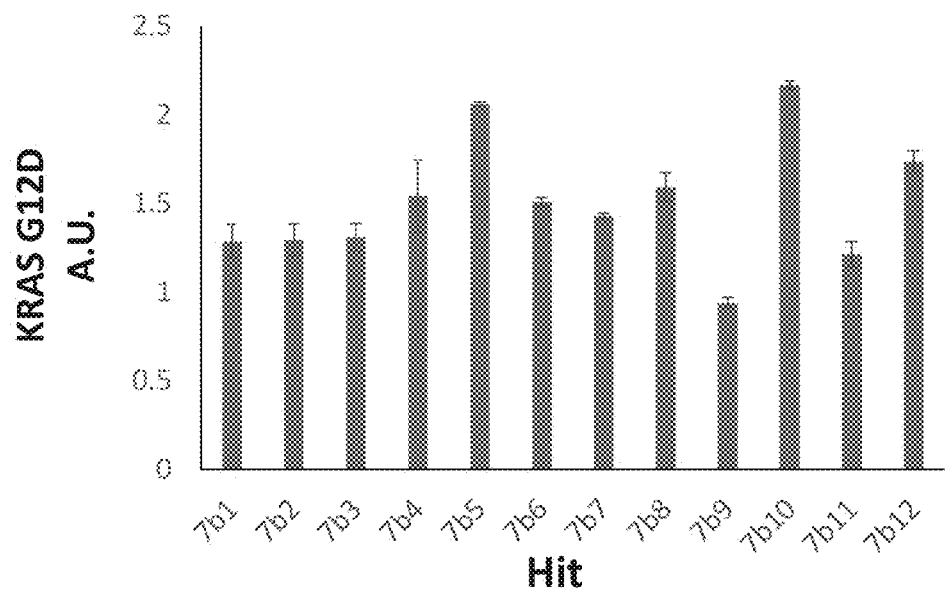
FIG. 19A is a graph of the relative absorbance units (A.U.) from an ELISA assay measuring binding to K-Ras G12D in the presence of the indicated biotin-tagged cyclic peptide, according to embodiments of the present invention.
Figure 19B:
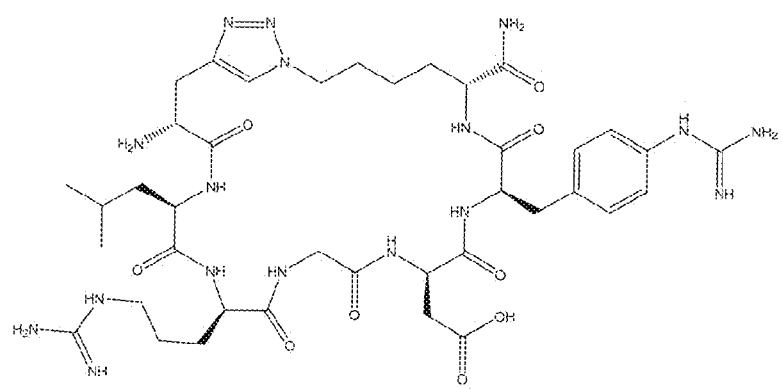
FIG. 19B shows the Formula 1 structure of cyclic peptide 7b10 (Pra-LRGD(guanidinoF)-Az4), according to embodiments of the present invention.
Figure 20A:
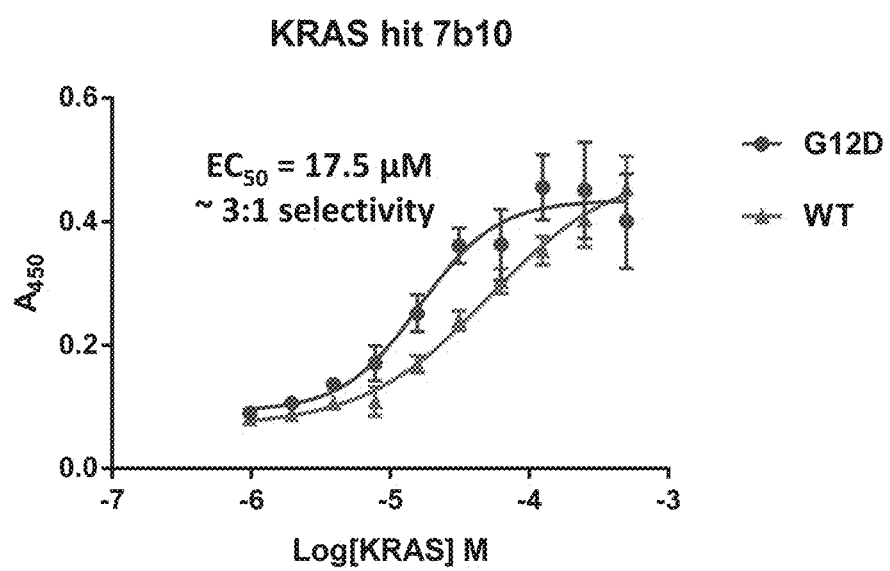
FIG. 20A is a graph of an ELISA binding assay of K-Ras G12D (blue) and WT K-Ras (red) with cyclic peptide 7b10, in which cyclic peptide 7b10 has an $EC_{50}$ binding value of 17.5 µM against K-Ras G12D and 55.6 µM for WT K-Ras, for a 3:1 selectivity of K-Ras G12D, according to embodiments of the present invention.
Figure 20B:
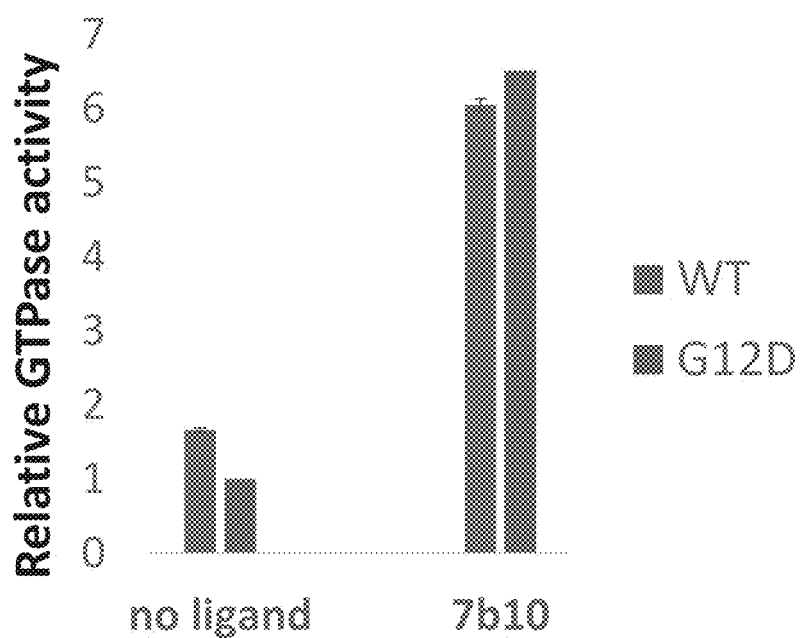
FIG. 20B is a graph showing the relative GTP hydrolysis (GTPase activity) of WT K-Ras (blue) and K-Ras G12D (red) proteins incubated with GTP alone (no ligand) or GTP and cyclic peptide 7b10 (7b10), in which the GTP hydrolysis was measured by detecting free phosphate with malachite green and measuring the absorbance at 620 nm, according to embodiments of the present invention.
Figure 21:
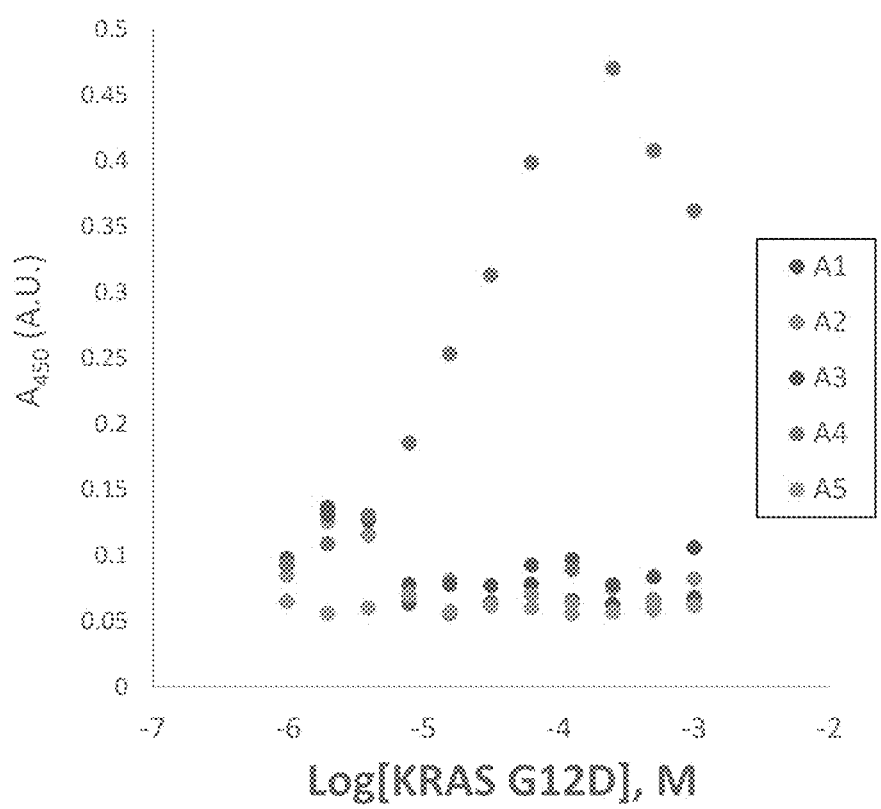
FIG. 21 is a graph of the amount of absorbance units (A.U.) in an ELISA assay measuring the binding to K-Ras G12D in the presence of alanine-substituted cyclic peptide 7b10, in which alanine (A) was substituted in each position of the X variable region, giving cyclic peptides 7b10-A1 (A1) (red), 7b10-A2 (A2) (green), 7b10-A3 (A3)(purple), 7b10-A4 (A4)(blue), and 7b10-A5 (A5)(orange), where only 7b10-A4 maintained its binding affinity for K-Ras G12D, according to embodiments of the present invention.

In some embodiments of the present invention, the cyclic peptide of Formula 1 may include $B_m$ representing a detection moiety, where m is 0 or 1. The detection moiety includes an optional spacer group and a detection tag. In some embodiments, when m is 1, B may be a spacer group, a detection tag, or a conjugate of both a spacer group and a detection tag. In some embodiments, the detection moiety may be conjugated to any group of the cyclic peptide. In some embodiments, the detection moiety (B) is conjugated to the C-terminus of Z2. For example, as shown in FIG. 5A, the detection moiety is conjugated to the C-terminus of Az4.

In some embodiments of the present invention, non-limiting examples of a spacer group include polyethylene glycol (PEG)n or 6-aminohexanoic acid (Ahx). As known to one of ordinary skill in the art, the number of PEG units (n) (or ethylene glycol repeats) determines the length of the spacer group. For example, 2 PEG units provide a spacer length of 18 angstroms. In some embodiments of the present invention, the spacer group includes 2 to 24 PEG units, 2 to 20 PEG units, 2 to 15 PEG units, 2 to 10 PEG units, 2 to 5 PEG units, 2 to 4 PEG units, or 2 to 3 PEG units.

As used herein, "tag," "detection tag," and like terms refer to a covalently linked chemical moiety that may be selectively bound and isolated. In some embodiments, "tag" refers to an "affinity tag" in which the chemical moiety has a specific binding partner. Non-limiting examples of affinity tags include biotin, streptavidin, poly-histidine (6-HIS) (SEQ ID NO: 39), poly-arginine (5-6 R) (SEQ ID NO: 40), FLAG, cyclodextrin, adamantane, and combinations thereof. Affinity tags for labeling peptides are described, for example in K. Terpe, 2003, *Appl. Microbiol. Biotechnol*, 2003, 60:523-533, the entire contents of which are incorporated herein by reference. In some embodiments, the detection tag may be a fluorescent dye or may be a fluorescent dye conjugated to an affinity tag.

The cyclic peptides according to embodiments of the present invention may be prepared by procedures known to those of skill in the art. For example, the cyclic peptides may be prepared using standard solid-phase peptide synthesis (SPPS) techniques as described for example, in Das et al. 2015, *Angew. Chem. Int. Ed.*, 54: 1329-13224, the entire contents of which is incorporated herein by reference. Methods for synthesizing and cyclizing the peptides using azide/alkyne chemistry are described in more detail in the examples.

Wild Type and G12D K-Ras Synthetic Epitopes for Click Chemistry

In some embodiments of the present invention, synthetic epitopes of wild type K-Ras TEYKLVVVGAGG[Z1]GK-SALTIQ (SEQ ID NO: 25) and oncogenic K-Ras G12D TEYKLVVVGADG[Z1]GKSALTIQ (SEQ ID NO: 26) include an azide amino acid (Z1). In some embodiments, Z1 is Pra, OrnN3 or AZ4 as described herein. These azide-modified WT and G12D K-Ras epitopes provide a click handle for covalently linking the epitope with binding partners (e.g., peptides) isolated from the azide cyclic peptide library as disclosed in Das et al. supra, and the examples herein.

Cyclic Peptide Binding to KRas G12D in Cellulo

In some embodiments of the present invention, a method for inhibiting the oncoprotein K-Ras G12D includes treating cancer cells having the K-Ras G12D mutation with a cyclic peptide of Formula 1 as disclosed herein. As shown in FIG. 24, cyclic peptide 7b5 conjugated to a proteasome degradation sequence (Hif) is capable of decreasing or depleting levels of K-Ras G12D in pancreatic cancer cells as shown by Western blot analysis of a pancreatic cell lysate after the cells were incubated with 7b5, a 7b5-Hif conjugate, and a 7b5-Hif-HIV TAT conjugate having a cell penetrating sequence as described herein. In some embodiments of the present invention, a cyclic peptide of Formula I may be used to inhibit K-Ras G12D expressed in any cancer cell. For example, the K-Ras G12D oncoprotein has been identified in pancreatic, colorectal, lung, biliary tract, and ovarian cancer cells.

The following Examples are presented for illustrative purposes only, and do not limit the scope or content of the present application.

EXAMPLES

Example 1. In Situ Click Screen

To screen for the cyclic peptides that selectively bind K-Ras G12D, an epitope-targeting strategy was used that identifies high-affinity protein catalyzed capture (PCC) agents against a specific region of interest in a protein using in situ click chemistry as depicted in FIG. 1 and described in Nag et al., 2013, *Angew. Chem. Int. Ed.* 52:13975-13979, the entire contents of which are incorporated herein by reference. Modified K-Ras wild type and G12D epitopes were synthesized with acetylene-functionalized amino acids for use in the in situ click screen (FIG. 1). The epitopes were derived from amino acids 2-22 from the K-Ras protein sequence with valine 14 substituted with propargylglycine (Pra). Additionally, an 11-unit polyethylene glycol (PEG) spacer and biotin were added to the C-terminus of the synthesized fragments for detection with streptavidin during the screen. The sequence of the wild type K-Ras epitope fragment was NH2-TEYKLVVVGAGG[Pra]GK-SALTIQ (SEQ ID NO: 21)-Peg11-Biotin. The sequence of the G12D fragment was NH2-TEYKLVVVGADG[Pra]GKSALTIQ (SEQ ID NO: 22)—Peg11-Biotin. The epitopes were synthesized by solid phase peptide synthesis (SPPS) on biotin novatag resin according to standard protocols.

The one-bead-one-compound (OBOC) cyclic peptide library is a 7-amino acid macrocyclic library with a 5-amino acid variable region (FIG. 1) The library peptides contain a C-terminal azidolysine followed by the 5-mer variable region and an N-terminal propargylglycine. A copper catalyzed click reaction was then used to cyclize the resin-bound peptides through the side chains of the N- and C-terminal residues. Finally, azidolysine was added to the N-terminus of the cyclized library to serve as a click handle for the in situ click screen. The library was synthesized by SPPS on tentagel resin according to standard protocols.

Figure 2:
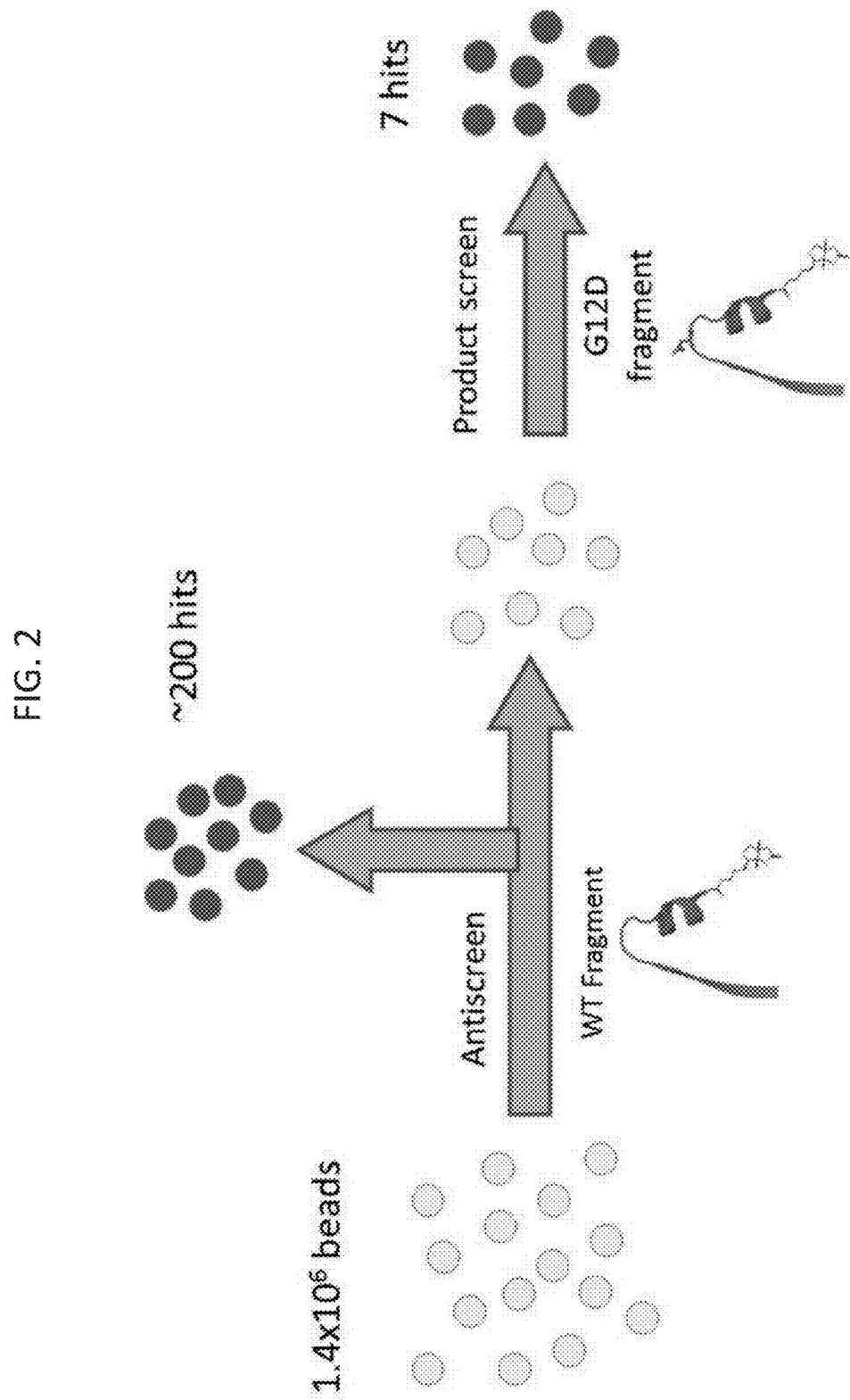
FIG. 2 is a schematic, for the in situ click chemistry screen as shown in FIG. 1, where the cyclic peptide library is first precleared in an "antiscreen" with a wild-type (WT) K-Ras epitope fragment to remove the peptide hits that bind to this non-cancerous (WT) form of the K-Ras protein, with the remaining cyclic peptide library beads used in the "product screen" against the K-Ras G12D epitope to identify cyclic peptides (7 hits) that bind selectively to this oncogenic epitope of K-Ras.
Figure 4A:
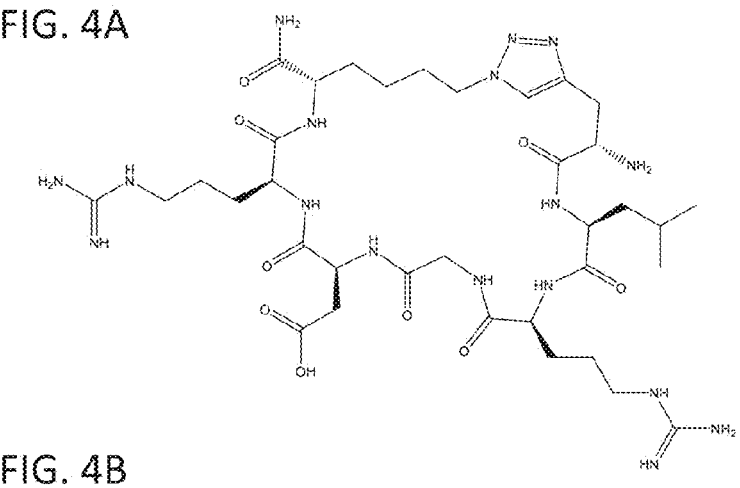
FIG. 4A shows the Formula 1 structure of cyclic peptide 7b (Pra-LRGDR-Az4 (SEQ ID NO: 27)), according to embodiments of the present invention.
Figure 4B:
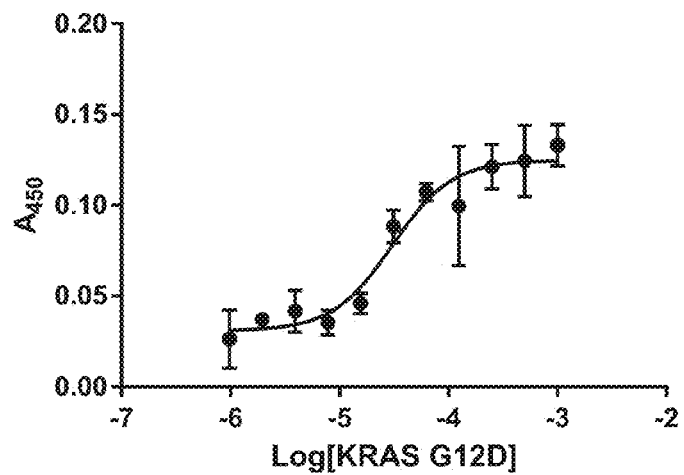
FIG. 4B is a graph of an ELISA binding assay in which cyclic peptide 7b has an $EC_{50}$ binding value of 33.3 µM against K-Ras G12D, according to embodiments of the present invention.
Figure 4C:
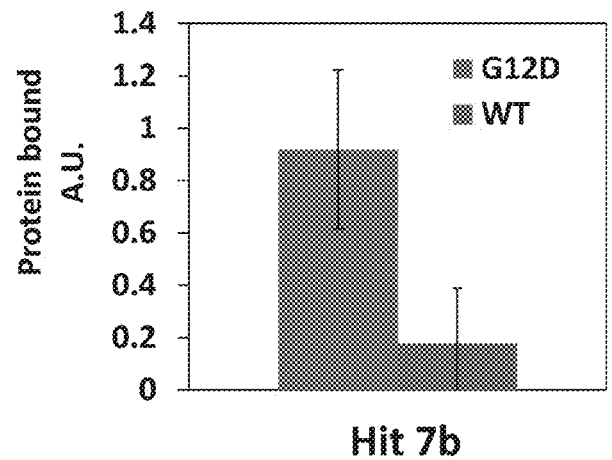
FIG. 4C is a graph of a single point ELISA assay comparing the binding (measured in absorbance units, A.U.) of cyclic peptide 7b to WT K-Ras (red bar) and K-Ras G12D (blue bar), according to embodiments of the present invention.

This azide (OBOC) peptide library has $1.4 \times 10^6$ unique members (FIG. 2) Approximately 200 hits (peptides that bind to the target epitope) clicked to the wild-type K-Ras fragment in the antiscreen, and were removed from the screen in order to avoid selecting hits that bind to the wild type K-Ras. The remaining beads were then incubated in a product screen with K-Ras G12D propargyl glycine-functionalized K-Ras G12D fragment (V14Pra), and 7 hits were isolated resulting in 9 possible sequences. The hits were sequenced using N-terminal Edman degradation and two of the beads each resulted in two possible sequences, resulting in SEQ ID NOs: 1-9 as listed in Table 1 and FIG. 3A.

Example 2. Synthesis of Hit Compounds

Hit peptides were synthesized following the same procedure as the library synthesis using SPPS. Briefly, the linear sequence Pra-$X_1X_2X_3X_4X_5$-Az4 was synthesized on PEG-Biotin Novatag resin (EMD Millipore) using standard solid phase peptide synthesis followed by copper catalyzed cyclization between Pra and Az4. The dried resin was then treated with a TFA cleavage solution of 95% TFA, 2.5% H2O, and 2.5% triethylsilane for two hours at room temperature. The cleavage solution was filtered to remove the resin and added dropwise to an ice-cooled solution of diethyl ether. All peptides were purified using a preparative or semi-preparative scale high performance liquid chromatography (HPLC) with a C18 reverse phase column. A gradient of double distilled water and HPLC grade acetonitrile and 0.1% TFA was used for all purifications.

Example 3. Screen Hit Peptides Against Full-Length K-Ras/K-Ras G12D

The nine sequences were tested for binding to K-Ras (G12D) by enzyme-linked immunosorbent assay (ELISA) (FIG. 3B). The cyclic peptide 7b having variable region LRGDR (SEQ ID NO: 7), showed the highest affinity and selectivity binder for G12D K-Ras over WT K-Ras. As shown in FIG. 3B, cyclic peptides having amino acid variable regions SEQ ID NOs: 1-9, bind to K-Ras G12D, and cyclic peptide 7b binds with the highest affinity for K-Ras G12D. Cyclic peptide 7b includes the sequence Pra-LRGDR-Az4 (SEQ ID NO: 27).

Example 4. Modified 7b Variants

In order to improve upon the binding of 7b to K-Ras G12D, further variants of 7b were synthesized (7b1-7b12, 7b14) each of which is listed in Table 2 and shown in FIGS. 5A-17A. As shown respectively in each of FIGS. 5A-17A, cyclic peptides 7b1-7b12 and 7b14 include the These 7b variant cyclic peptides were assayed for binding to K-Ras G12D in ELISA assays as shown in FIGS. 18a-19A.

Example 5. Degradation of K-Ras G12D Using Cyclic Peptides

Figure 22A:
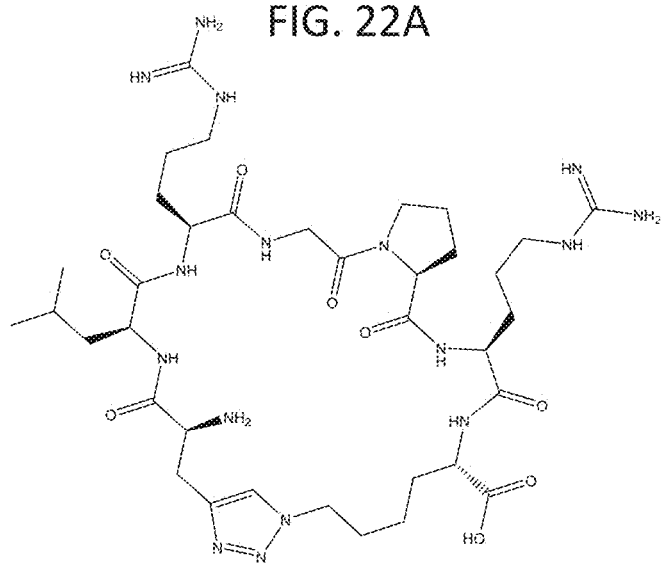
FIG. 22A shows the Formula 1 structure of cyclic peptide 7b5 (Pra-LRGPR-Az4 (SEQ ID NO: 31)), according to embodiments of the present invention.
Figure 22B:
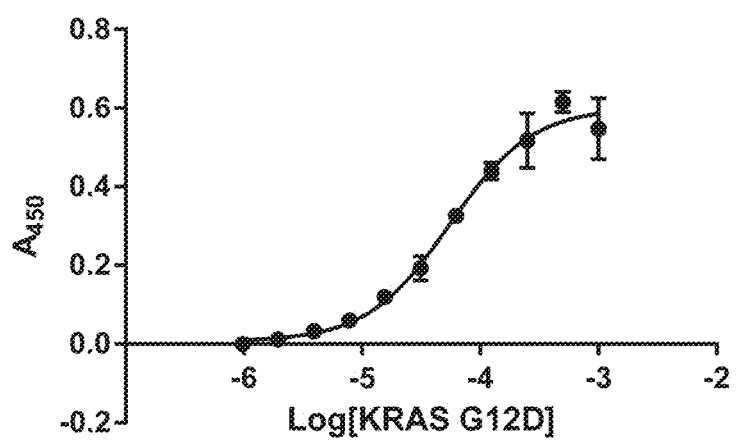
FIG. 22B is a graph of an ELISA binding assay in which cyclic peptide 7b5 has an $EC_{50}$ binding value of 56.6 μM against K-Ras G12D, according to embodiments of the present invention.
Figure 23:
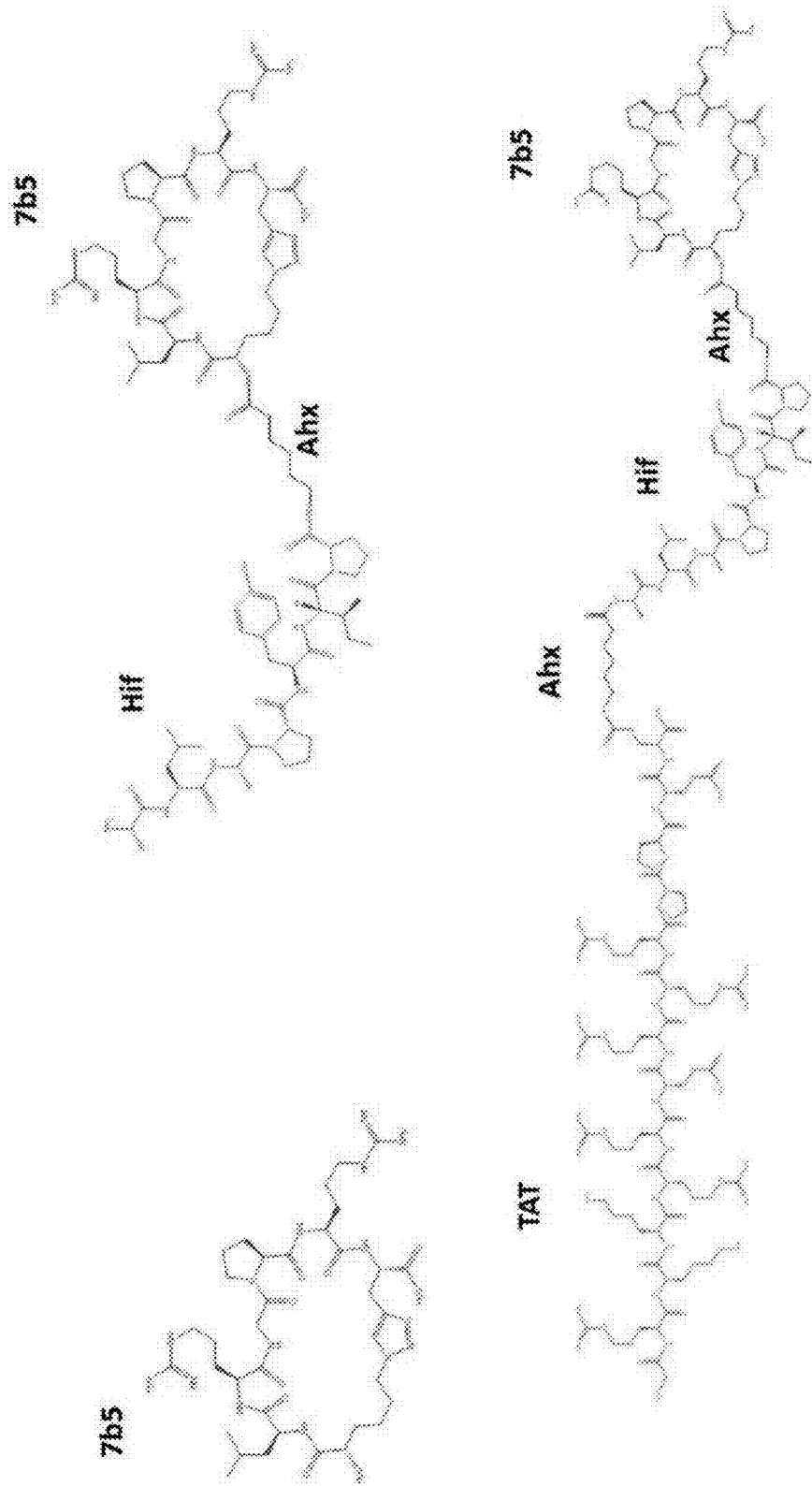
FIG. 23 shows the structure of cyclic peptide 7b5 (blue) alone and conjugated to 7-amino acid sequence ALAPYIP (SEQ ID NO: 23) (Hif)(green) via a 6-aminohexanoic acid linker (Ahx)(black), and 7b5 (blue) conjugated to Hif (green) via the Ahx linker (black) with the Hif moiety conjugated to HIV-TAT peptide (GRKKRRQRRRPPQQ) (SEQ ID NO: 24)(red), according to embodiments of the present invention.
Figure 24A:
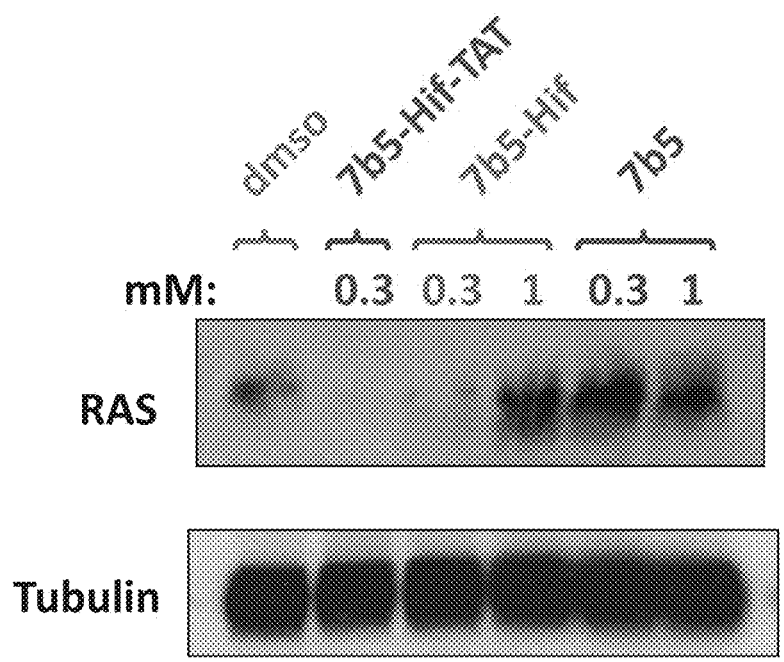
FIG. 24A shows a Western blot analysis of Ras G12D protein in Panc 08.13 cancer cells (homozygous for K-Ras G12D) after treatment with DMSO (control), 7b5-Hif-TAT, 7b5-Hif, and 7b5, as indicated, in which the cells treated with 7b5-Hif and 7b5-Hif-TAT show depletion of Ras protein, according to embodiments of the present invention.
Figure 24B:
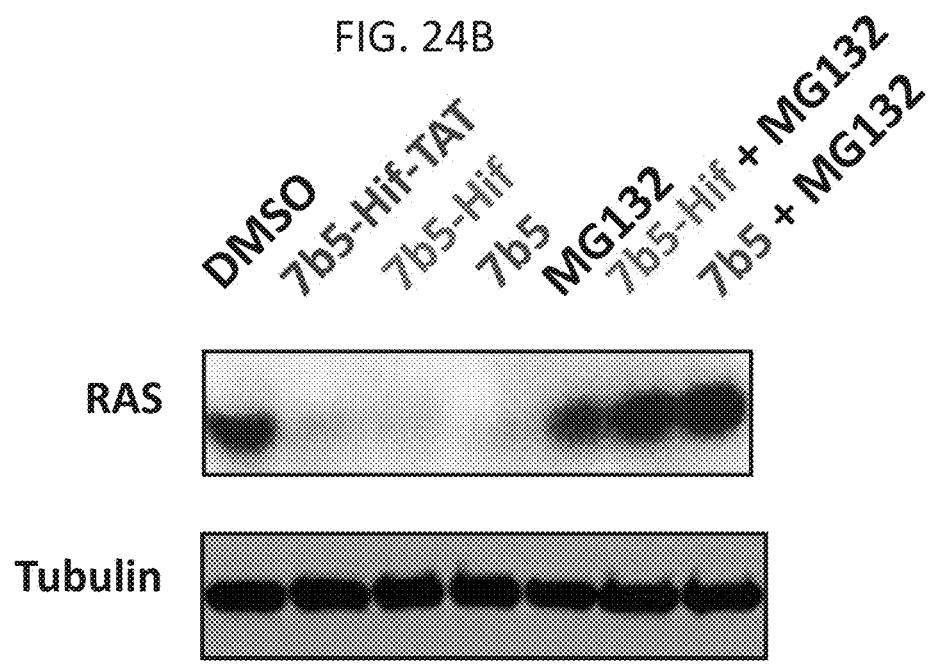
FIG. 24B shows a Western blot analysis of Ras G12D protein in Panc 08.13 cancer cells after similar treatment conditions as in FIG. 24A, except that where indicated, cells were pretreated with the proteasome inhibitor MG132 followed by the incubation with DMSO, 7b5-Hif, or 7b5, showing that when the proteasome is inhibited, the Ras protein is not depleted in the presence of 7b6-Hif, according to embodiments of the present invention.

Cyclic peptide 7b5 was shown to induce proteasomal degradation of K-Ras G12D in pancreatic cancer cells. The 7b5 peptide (FIG. 22A-22B) was functionalized with the degradation-inducing sequence ALAPYIP (SEQ ID NO: 23) from the protein Hif-1α. Proteolysis-targeting chimeras (PROTACs) using Hif and other proteins are described in Toure and Crews, 2016, *Angew. Chem. Int. Ed,* 55:2-10, the entire contents of which are incorporated herein by reference. The 7b-Hif PROTAC was further conjugated with the HIV-TAT cell-penetrating peptide GRKKRRQRRRPPQQ (SEQ ID NO: 24). Structures of 7b5, 7b5-Hif, 7b5-Hif-TAT are shown in FIG. 23. Panc 08.13 cancer cells which are homozygous for the K-Ras G12D mutation were treated with cyclic peptide 7b5, 7b5-Hif, or 7b6-Hif-TAT for 30 minutes followed by cell lysis. The cell lysates were analyzed by Western blot for levels of K-Ras G12D protein as shown in FIG. 24A. The levels of K-Ras G12D were decreased (or depleted) in the presence of 0.3 mM 7b5-Hif-TAT and 7b5-Hif. By pretreating the Panc 08.13 cells with the proteasome inhibitor MG132, the K-Ras G12D depletion of 7b5-Hif was prevented.\

Example 6. Materials and Methods

In situ cyclic peptide library screen as previously described in Das et al. 2015, *Angew. Chem. Int. Ed.,* 54: 1329-13224, the entire contents of which is incorporated herein by reference. Anchor screen conditions: screen against 500 mg (approximately 1,400,000) beads of 5-mer (comprehensive library). Library includes Az4-[Pra]-A1A2A3A4A5-[Az4]-[100% Met]-TG, where A is 18 amino acids (no D-Cys, no D-Met), [Pra] and [Az4] are connected via a 1,4-triazole linkage.
Step 1: Preclear: Swell library beads in TBS for 6 hours (h). Block overnight at 4° C. with 1% BSA in TBS with 0.1% Tween 20 (Blocking Buffer). Wash with Blocking Buffer (5 times (x)). The following day, add 1:10,000 anti-Biotin-AP Antibody (Sigma Aldrich) in Blocking Buffer. Incubate on shaking arm for 1 hour (h) at room temperature (RT). Wash: 5×3 mL Blocking Buffer, 5×3 mL Wash 1 buffer (0.1% BSA in TBS+0.1% Tween 20), then 5×3 mL Wash 2 buffer (TBS+0.1% Tween 20). Drain. Develop with BCIP: NBT (Promega #S3771). Remove purple beads as false hits (depending on how many beads are purple). Preparation of BCIP:NBT: For every 5 mL of Alkaline Phosphatase Buffer (100 mM Tris-HCl [pH 9.0], 150 mM NaCl, 1 mM MgCl2), add 33 µL NBT (50 mg/mL stock in 70% DMF) and 16.5 µL BCIP (50 mg/mL stock in 70% DMF). For remaining clear beads, wash with 7.5 M Gu-HCl, pH 2.0 for 30 min. Rinse with water 10 times. Incubate clear beads in NMP to remove trace purple coloring (a few hours). Wash with water, then TBS buffer. Block overnight at 4° C. with Blocking Buffer.
Step 2: Anti-screen against wild type KRAS polypeptide target. Use 50 µM (2% DMSO, v/v) concentration of Polypeptide. The Polypeptide will be consumed as a substrate of the in situ click reaction. For beads isolated in Step 1, wash with Blocking Buffer (3×3 min each (ea)). Combine Polypeptide solution with beads and incubate on shaking arm for 5 h at RT. Wash: 3 times with Blocking Buffer (3 min ea), then 10×TBS (3×3 min ea, then 7×0 min ea), and drain. Incubate beads for 1 h in 7.5 M Gu-HCl, pH 2.0. Wash 6 times with TBS (3×3 min ea, then 3×0 min ea). Block for 2 h at RT with Blocking Buffer. Wash with Blocking Buffer (5×0 min ea). Add 1:10,000 Anti-Biotin-AP in Blocking Buffer. Incubate on shaking arm for 1 h at RT. Wash with 5×3 mL Blocking Buffer, 5×3 mL Wash 1 buffer (3 mins ea), then 5×3 mL Wash 2 buffer (3 min ea), and drain. Develop with BCIP:NBT as described in Step 1. Pick purple hits. Wash hits with 7.5 M Gu-HCl, pH 2.0 for 30 min. Rinse with water 10 times. Incubate hits in NMP to remove purple coloring (a few hours). Wash with water, and then TBS. Block overnight at 4° C. with Blocking Buffer.
Step 3: Product screen against mutant KRAS G12D polypeptide target. Use 50 µM (2% DMSO, v/v) concentration of Polypeptide. The Polypeptide will be consumed as a substrate of the in situ click reaction. For beads isolated in Step 1, wash with Blocking Buffer (3×3 min ea). Combine Polypeptide solution with beads and incubate on shaking arm for 5 h at RT. Wash with Blocking Buffer 3 times, 3 min ea, and then 10 times with TBS (3×3 min ea, then 7×0 min ea), and drain. Incubate beads for 1 h in 7.5 M Gu-HCl, pH 2.0. Wash 6 times with TBS (3×3 min ea, then 3×0 min ea). Block for 2 h at RT with Blocking Buffer. Wash with Blocking Buffer (5 times). Add 1:10,000 Anti-Biotin-AP in Blocking Buffer. Incubate on shaking arm for 1 h at RT. Wash: 5×3 mL Blocking Buffer, 5×3 mL Wash 1 buffer (3 mins ea), then 5×3 mL Wash 2 buffer (3 min ea), and drain. Develop with BCIP:NBT as described in Step 1. Pick purple hits Wash hits with 7.5 M Gu-HCl, pH 2.0 for 30 min, and rinse with water 10 times. Incubate hits in NMP to remove purple coloring (a few hours). Wash with water, and then TBS. Sequence hit beads via Edman degradation
ELISA Assays.
For ELISA assays, 1 µM of the biotinylated hit peptides were first immobilized onto Neutravidin ELISA plates (Pierce) for 2 hours at room temperature in binding buffer (TBST with 0.1% BSA). The plates were then blocked with 5% BSA for 1 hour, followed by incubating with varying concentrations of wild type or G12D KRAS for 30 minutes. After washing three times with TBST the plate was then treated with a 1:1000 dilution of the anti-RAS rabbit mAb (Cell Signaling Technology) in binding buffer for thirty minutes, washed three times with TBST, incubated with anti-Rabbit-HRP secondary antibody (Cell Signaling Technology) for thirty minutes and developed with TMB substrate (KPL) for five to ten minutes. The absorbance of samples at 450 nm wavelength was measured using a spectrophotometer.

Mass Spectrometry Analysis.

Peptides were characterized via MALDI-TOF-MS using a Voyager DE-PRO MALDI TOF-MS system (Applied Biosystems). Crude or purified samples were dissolved in 50:50 water/acetonitrile with 0.1% trifluoroacetic acid at a final concentration of 10 pmol/μL. 1 μL of the analyte sample was then added to 10 μL of a saturated solution of MALDI matrix, either α-cyano-4-hydroxycinnamic acid or Sinapinic Acid, in 50:50 water/acetonitrile with 0.1% trifluoroacetic acid and analyzed via MALDI-TOF MS.

Cell Culture.

Panc 08.13 cell lines were purchased from American Type Culture collection and cultured as specified by the provider.

Immunoblotting.

Western blots were performed according to standard protocols. Briefly, cells were lysed with cell lysis buffer (Cell Signaling Technology) containing protease and phosphatase inhibitors (Cell Signaling Technology). Cell lysates were quantified with a Bradford protein assay (Thermo Scientific) and prepared for gel electrophoresis in Laemmli sample buffer and reducing agent. 20 μg of cell lysate were added to precast polyacrylamide gels (Bio-Rad) and proteins were separated by electrophoresis followed by transfer to PVDF membrane. Membranes were then blocked and probed with an anti-Ras or anti-Tubulin primary antibody followed by horseradish peroxidase-conjugated secondary antibody (Cell Signaling Technology). The bands were visualized by chemiluminescence (Thermo Scientific).

As disclosed throughout, for example in Tables 1 and 2, and FIGS. 5A-17A, 19A, and 24A-24B, cyclic peptides of Formula 1 are capable of selectively binding the oncoprotein K-Ras G12D in vitro and in cellulo.

While the present invention has been illustrated and described with reference to certain exemplary embodiments, those of ordinary skill in the art will understand that various modifications and changes may be made to the described embodiments without departing from the spirit and scope of the present invention, as defined in the following claims.

---

What is claimed is:

1. A cyclic peptide represented by Formula I:

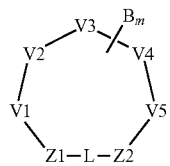

wherein: Z1 and Z2 are each L-propargylglycine (Pra), azidoornithine (OrnN3), or L-azidolysine (Az4), wherein when Z1 is Pra, Z2 is OrnN3 or Az4, when Z1 is OrnN3 or Az4, Z2 is Pra; and V1-V2-V3-V4-V5 is a five amino acid variable region having a sequence selected from the group consisting of SEQ ID NOs: 1-20; L is a linker moiety; and $B_m$ is an optional detection group, wherein m is 0 or 1.

2. The cyclic peptide of claim 1, wherein Z1 is Pra and Z2 is Az4.

3. The cyclic peptide of claim 1, wherein Z1 is Pra and Z2 is OrnN3.

4. The cyclic peptide of claim 1, wherein Z1 is Az4 and Z2 is Pra.

5. The cyclic peptide of claim 1, wherein V1-V2-V3-V4-V5 is SEQ ID NO: 7, 11, or 16.

6. The cyclic peptide of claim 1, wherein L is 1,4-triazole.

7. The cyclic peptide of claim 6, wherein when m is 1, the optional detection group is a detection tag, a detection tag, or a combination of a spacer group and a detection tag.

8. The cyclic peptide of claim 7, wherein the spacer group is polyethylene glycol (PEG) or 6-aminohexanoic acid (Ahx).

9. The cyclic peptide of claim 7, wherein the detection tag is an affinity tag, a fluorescent tag, or a fluorescently labeled affinity tag.

10. The cyclic peptide of claim 7, wherein the detection tag is an affinity tag selected from the group consisting of biotin, streptavidin, poly-histidine, poly-arginine, FLAG, cyclodextrin, adamantane, and combinations thereof.

11. The cyclic peptide of claim 7 wherein the spacer group is PEG and the detection tag is biotin.

* * * * *